US009783838B2

(12) United States Patent
Chen et al.

(10) Patent No.: US 9,783,838 B2
(45) Date of Patent: Oct. 10, 2017

(54) PMST3 ENZYME FOR CHEMOENZYMATIC SYNTHESIS OF ALPHA-2-3-SIALOSIDES

(71) Applicant: The Regents of the University of California, Oakland, CA (US)

(72) Inventors: Xi Chen, Davis, CA (US); Vireak Thon, San Francisco, CA (US); Hai Yu, Woodland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/356,376

(22) PCT Filed: Nov. 7, 2012

(86) PCT No.: PCT/US2012/063826
§ 371 (c)(1),
(2) Date: May 5, 2014

(87) PCT Pub. No.: WO2013/070677
PCT Pub. Date: May 16, 2013

(65) Prior Publication Data

US 2014/0349339 A1 Nov. 27, 2014

Related U.S. Application Data

(60) Provisional application No. 61/556,620, filed on Nov. 7, 2012, provisional application No. 61/585,381, filed on Jan. 11, 2012.

(51) Int. Cl.
*C12P 21/00* (2006.01)
*C12P 19/18* (2006.01)
(Continued)

(52) U.S. Cl.
CPC .......... *C12P 21/005* (2013.01); *C12N 9/1051* (2013.01); *C12N 9/1081* (2013.01);
(Continued)

(58) Field of Classification Search
CPC ......... C12P 21/005; C12P 19/18; C12P 19/26; C12P 19/44; C12N 9/1051; C12N 9/1081
See application file for complete search history.

(56) References Cited

U.S. PATENT DOCUMENTS 5,334,514 A * 8/1994 Kittelmann et al. ............ 435/84
5,374,541 A 12/1994 Wong et al.
(Continued)

FOREIGN PATENT DOCUMENTS

EP WO2008040717 * 4/2008

OTHER PUBLICATIONS

Zhao et al. Real time Measurement of Metabolic States in Living Cells using Genetically-encoded NADH Sensors., Methods Enzymol. (2014), vol. 542, pp. 349-367.*
(Continued)

*Primary Examiner* — Alexander Kim
(74) *Attorney, Agent, or Firm* — Kilpatrick Townsend and Stockton LLP

(57) ABSTRACT

The present invention provides novel methods for preparing glycosylated molecules such as oligosaccharides, glycolipids, and glycoproteins/peptides. Novel sialyltransferases are also disclosed. The method includes forming a reaction mixture containing an acceptor molecule, a donor substrate having a sugar moiety and a nucleotide, and a sialyltransferase selected from PmST3 (SEQ ID NO:7) and certain variants thereof. The reaction mixture is formed under conditions sufficient to transfer the sugar moiety from the donor substrate to the acceptor molecule, thereby forming the glycosylated molecule. In some embodiments, the acceptor molecule is selected from a natural product, an oligosaccharide, a glycoprotein, and a glycolipid. In some embodiments, the donor substrate is formed via conversion of a suitable hexosamine derivative to a cytidine 5'-monophos-
(Continued)

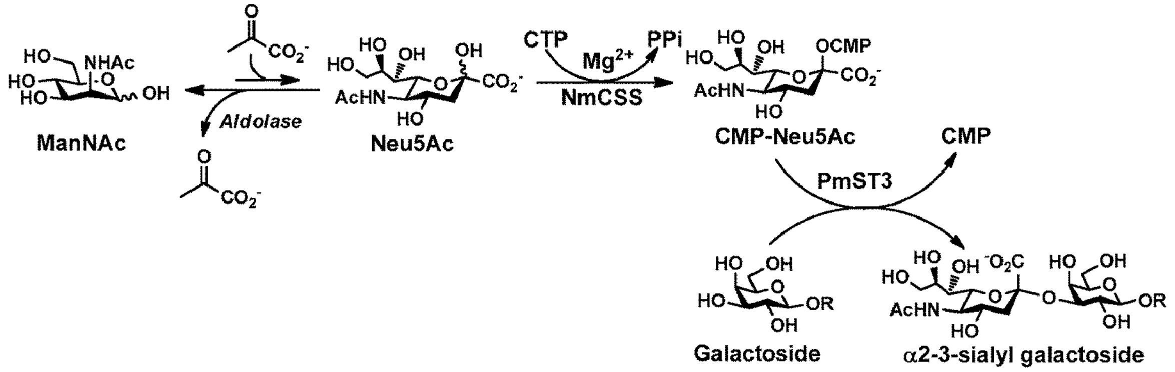

ManNAc Neu5Ac CMP-Neu5Ac Galactoside α2-3-sialyl galactoside phate(CMP)-sialic acid in a one-pot reaction mixture containing asialic acid aldolase and a CMP-sialic acid synthetase.

17 Claims, 7 Drawing Sheets

(51) Int. Cl.
*C12P 19/26* (2006.01)
*C12P 19/44* (2006.01)
*C12N 9/10* (2006.01)
(52) U.S. Cl.
CPC ............... *C12P 19/18* (2013.01); *C12P 19/26* (2013.01); *C12P 19/44* (2013.01)

(56) References Cited

U.S. PATENT DOCUMENTS

| | | | | |
|---|---|---|---|---|
| 2005/0089956 | A1* | 4/2005 | Endo et al. | 435/69.1 |
| 2007/0275908 | A1 | 11/2007 | Defrees et al. | |
| 2009/0215115 | A1 | 8/2009 | Gilbert et al. | |
| 2010/0291631 | A1 | 11/2010 | Yamamoto et al. | |

OTHER PUBLICATIONS

Gautam et al., Exterior design: strategies for redecorating the bacterial surface with small molecules., Trends in Biotechnology (2013), vol. 31, pp. 258-267.*
Norman et al., Sialyl Lewisx (sLex) and an sLexMimetic, CGP69669A, Disrupt E-Selectin-Dependent Leukocyte Rolling In Vivo., Blood (1998), vol. 91 (2), pp. 475-483.*
Lacto-n-biose (last viewed on May 9, 2016).*
Galacto-N-biose (last viewed on May 9, 2016).*
Sujino et al., A novel viral α2,3-sialyltransferase (v-ST3Gal I): transfer of sialic acid to fucosylated acceptors., Glycobiology (2000), vol. 10, pp. 313-320.*
International Search Report & Written Opinion for PCT/US2012/063826 dated Apr. 8, 2013.
Audry et al., "Current trends in the structure-activity relationships of sialyltransferases," Glycobiology, 2011, vol. 21(6), pp. 716-726.
Cheng et al., "Multifunctionality of Campylobacter jejuni sialyltransferase CstII: Characterization of GD3/GT3 oligosaccharide synthase, GD3 oligosaccharide sialidase, and trans-sialidase activities," Glycobiology, 2008, vol. 18(9), pp. 686-697.
Chung et al., "Vaccination against fowl cholera with acapsular Pasteurella multocida A:1," Vaccine, 2005, 23: 2751-2755.
Coutinho et al., "An evolving hierarchical family classification for glycosyltransferases," J Mol Biol., 2003, vol. 328, pp. 307-317.
Gilbert et al., "Characterization of a recombinant Neisseria meningitides alpha-2,3-sialyltransferase and its acceptor specificity," Eur J Biochem., 1997, 249: 187-194.
Gilbert et al., "Cloning of the lipooligosaccharide alpha-2,3-sialyltransferase from the bacterial pathogens *Neisseria meningitidis* and *Neisseria gonorrhoeae*," J Biol Chem., 1996, 271:28271-28276.
Izumi et al., "Microbial glycosyltransferases for carbohydrate synthesis: Alpha-2,3-sialyltransferase from *Neisseria gonorrheae*," J Am Chem Soc., 2001, 123:10909-10918.
Kakuta et al., "Crystal structure of *Vibrionaceae photobacterium* sp. JT-ISH-224 α2,6-sialyltransferase in a ternary complex with donor product CMP and acceptor substrate lactose: catalytic mechanism and substrate recognition," Glycobiology, 2008, vol. 18(1), pp. 66-73.
Kim et al., "Structural analysis of sialyltransferase PM0188 from Pasteurella multocida complexed with donor analogue and acceptor sugar," BMB Reports, 2008, vol. 41(1), pp. 48-54.
Kushi et al., "Sialyltransferases of marine bacteria efficiently utilize glycosphingolipid substrates," Glycobiology, 2010, 20:187-198.
Lairson et al.,"Glycosyltransferases: Structures, Functions, and Mechanisms," Annu. Rev. Biochem., 2008, vol. 77, pp. 521-555.
Larsson et al., "Synthesis of reference standards to enable single cell metabolomic studies of tetramethylrhodaminelabeled ganglioside GM1," Carbohydr Res., 2007, 342:482-489.
Li et al., "The Hd0053 gene of Haemophilus ducreyi encodes an alpha2,3-sialyltransferase," Biochem Biophys Res Commun, 2007, vol. 361(2), pp. 555-560.
Li et al., "Sialic acid metabolism and sialyltransferases: natural functions and applications," Appl. Microbiol. Biotechnol., 2012, vol. 94, pp. 887-905.
Liu et al., "A striking example of the interfacing of glycal chemistry with enzymatically mediated sialylation: A concise synthesis of ganglioside GM3," J Am Chem Soc., 1993, 115:4933-4934.
May et al., "Complete genomic sequence of Pasteurella multocida, Pm70," Proc Natl Acad Sci USA, 2001, 98:3460-3465.
Ni et al., "Cytidine 5'-monophosphate (CMP)-induced structural changes in a multifunctional sialyltransferase from Pasteurella multocida," Biochemistry, 2006, 45:2139-2148.
Nishimura et al., "Transfer of ganglioside GM3 oligosaccharide from a water soluble polymer to ceramide by ceramide glycanase. A novel approach for the chemical-enzymatic synthesis of glycosphingolipids," J Am Chem Soc., 1997, 119:10555-10556.
Steenbergen et al., "Sialic acid metabolism and systemic pasteurellosis," Infect Immun., 2005, 73:1284-1294.
St. Michael et al., "Structural analysis of the lipopolysaccharide from Pasteurella multocida genome strain Pm70 and identification of the putative lipopolysaccharide glycosyltransferases," Glycobiology, 2005, 15:323-333.
Yu et al., "A multifunctional Pasteurella multocida sialyltransferase: A powerful tool for the synthesis of sialoside libraries," J Am Chem Soc., 2005, 127:17618-17619.
Zehavi et al., "Enzymic glycosphingolipid synthesis on polymer supports. III. Synthesis of G(M3), its analog [NeuNAc alpha(2-3) Gal beta(1-4)Glc beta(1-3)Cer] and their lyso-derivatives," Glycoconjugate J., 1998, 15:657-662.
International Search Report for PCT/US2012/049748, mailed Feb. 25, 2013, 4 pages.

* cited by examiner

FIG. 2A

```
Pm70        TCACAATCGCTTCAAATAATGGGGTCATATCTTCTGCTAAATCATCGTGTTCAAGACCCGCAACACCATTTAATG    1369314
P-1059                                                      *****-*********************
P-934       5' primer                                 ***********-*********************

Pm70        CAGAAGCATAAATAATTGGAAAATCTAACTGCTCATCAGTTGCACCTAAGTTGACAAAAAGATCAAAAACTTGAT    1369389
P-1059      *G*****************************G*****G*****************************G*******
P-934       *G***********************************G*************************************

Pm70        CCACTACCCAGTCAGGGCGCGCCCGGACGGTCAACTTTGTTGATCACCACAATTGGTTTTAAACCGTGGGCAA    1369464
P-1059      ****************A********A**************************T**********************
P-934       ****************A********A*****************A*******************************

Pm70        ACGCTTTTTGAGTCACAAAACGCGTTTGTGGCATTGGACCATCAAAAGCATCTACAATTAAAAGTACACAATCTA    1369539
P-1059      ***************************************************************************
P-934       ***************************************************************************

Pm70        CCATTGACATCACACGTTCCACTTCACCACCGAAGTCTGCGTGTCCTGGGGTGTCTACGATATTAATGCGATAGT    1369614
P-1059      *******************T*******************************************************
P-934       *******************T*******************************************************

Pm70        CATTCCAATTAATGGCGGTATTCTTAGCTAAAATGGTAATACCACGTTCTTTTTCGATGTCATTAGAGTCCATGA    1369689
P-1059      ***************************************************************************
P-934       ***************************************************************************

Pm70        CACGCTCATCACTTTCATTACGTGATGCCTCTAATGTGCCGGATTGTTGTAAAAGTTTATCAACGAGGGTAGTTT    1369764
P-1059      ***************************************************************************
P-934       ***************************************************************************

                                                  <-- Pm1173 gene coding sequence --|
Pm70        TACCGTGGTCAACGTGGGCGATAATTGCGATATTACGCAATTTATTGATATCTATTTTATCTGTCATTGAGAAAA    1369839
P-1059      ***************************************************************************
P-934       ***************************************************************************

Pm70        TCTTATATATTGAAATAGGAAAAAGTTCTTTTTCTGACCGCACTTTTAGCGAAAAAGTGTGTGAAAGGGGCAAGA    1369914
P-1059      ***************************************************************************
P-934       ***************************************************************************

                                                    |Pm1174 gene coding sequence
Pm70        TTATACAACAGATCCTCCCCCTAG-AGCCATAAAAACTGCTATTTTTCTTTTAAATAGTGTTTAAGTGCACTCGG... 1369988
P-1059      *********T--*TT*A*G**A**G******--------------------******A*----------------
P-934       *********T--*TT*A*G**A**G******--------------------******A*----------------

            <-- Pm1174 gene coding sequence|
Pm70    ... TATTTCATGTTCTGCGAACTTATCCATCTCTCCTCCACTAATTTATTATAGTGCATAATCCATGTATTCTACACG    1370912
P-1059      -----------------------------------****G*A-----*A*ACA*****-----AA*****GT---
P-934       -----------------------------------****G*A-----*A*ACA*****-----AA*****GT---

Pm70        AAATAAAGTGTAGGGATATATCCGAAAAACACGAATAAAATACTAGATTTATAGTATAACTTTTATTATATTGAA    1370987
P-1059      -----------------**T***C**-----***C*---------*T******A**---*****-****TC*--*
P-934       -----------------**T***C**-----***C*---------*T******A**---*****-****TC*--*

                                                   |Pm1175 gene coding sequence -->
Pm70        TTCTTTTAAATACGCTTCTAACACTAAGGAT--CCTCTATGTCAGACACCACCGCTATCGCCAACGTATTCAAGC    1371060
P-1059      C**CCCCA**-------******----****TT*T*A****C**A****AGTT**********************
P-934       C**CCCCA**-------****G*----****TT*T*A****C**A****AGTT**********************

Pm70        TGATTGAAGAATACGATATCAAATTTGTTTTACTTCGCTTTACCGATATTAAGGGGAAAGAACACGGTGTTTCGC    1371135
P-1059      **************A************************************************************
P-934       ***************************************************************************
```

FIG. 2B

```
Pm70     TTCCTGTTAATCTTGTTGATGAAGATTTATTTGAAGACGGTAAAATGTTCGACGGTTCTTCCGTTGAAGGATGGA    1371210
P-1059   ***************************************************************************
P-934    ***************************************************************************

Pm70     AGGCAATCAATAAAGCAGATATGCTCTTGATGCCAATGCCAGAAACAGCTGTGGTTGATCCTTTTGCTCAAATTC    1371285
P-1059   ***************************************************************************
P-934    **************C************************************************************

Pm70     CTACCCTTTCCCTCCGTTGCAGTATCTACGAACCTTCTACTATGCAAAGCTACGATCGTGATCCACGTTCTATTG    1371360
P-1059   ***************************************************************************
P-934    ***************************************************************************

Pm70     CGATTCGTGCAGAAAACTATATGCGTTCAACGGGAATAGCCGATGAAGCCCTCTTTGGGCCTGAACCAGAATTTT    1371435
P-1059   **********C***********************************************A****************
P-934    **********C***********************************************A*****G**********

Pm70     TCTTATTTGATGATGTTCGTTTCGATGTCTCGATGAACCGTAGCAGTTATTCTGTTGATGATATTGAGGCTGCGTGG  1371512
P-1059   *********************************
P-934    **********************************                                    3' primer
```

FIG. 3

```
ATGGATAAATTTGCCGAACATGAAATTCCGAAAGCCGTTATTGTTGCAGGTAATGGTGAA    60
 M  D  K  F  A  E  H  E  I  P  K  A  V  I  V  A  G  N  G  E     20

AGCCTGAGCCAGATTGATTATCGTCTGCTGCCGAAAAATTATGATGTGTTTCGCTGCAAT   120
 S  L  S  Q  I  D  Y  R  L  L  P  K  N  Y  D  V  F  R  C  N     40

CAGTTTTATTTTGAAGAACGCTATTTTCTGGGCAATAAAATTAAAGCCGTGTTTTTTACA   180
 Q  F  Y  F  E  E  R  Y  F  L  G  N  K  I  K  A  V  F  F  T     70

CCGGGTGTTTTTCTGGAACAGTATTATACCCTGTATCATCTGAAACGCAATAATGAATAT   240
 P  G  V  F  L  E  Q  Y  Y  T  L  Y  H  L  K  R  N  N  E  Y     80

TTTGTGGATAATGTGATTCTGAGCAGCTTTAATCATCCGACCGTTGATCTGGAAAAAAGC   300
 F  V  D  N  V  I  L  S  S  F  N  H  P  T  V  D  L  E  K  S    100

CAGAAAATTCAGGCCCTGTTTATTGATGTGATTAATGGCTATGAAAAATATCTGAGCAAA   360
 Q  K  I  Q  A  L  F  I  D  V  I  N  G  Y  E  K  Y  L  S  K    120

CTGACCGCCTTTGATGTTTATCTGCGCTATAAAGAACTGTATGAAAATCAGCGTATTACC   420
 L  T  A  F  D  V  Y  L  R  Y  K  E  L  Y  E  N  Q  R  I  T    140

AGCGGTGTTTATATGTGTGCAGTTGCAATTGCAATGGGCTATACCGATATTTATCTGACC   480
 S  G  V  Y  M  C  A  V  A  I  A  M  G  Y  T  D  I  Y  L  T    160

GGCATTGATTTTTATCAGGCCAGCGAAGAAAATTATGCCTTTGATAATAAAAAACCGAAT   540
 G  I  D  F  Y  Q  A  S  E  E  N  Y  A  F  D  N  K  K  P  N    180

ATTATTCGCCTGCTGCCGGATTTTCGCAAAGAAAAAACCCTGTTTAGCTATCATAGCAAA   600
 I  I  R  L  L  P  D  F  R  K  E  K  T  L  F  S  Y  H  S  K    200

GATATTGATCTGGAAGCCCTGAGCTTTCTGCAGCAGCATTATCATGTGAATTTTTATAGC   660
 D  I  D  L  E  A  L  S  F  L  Q  Q  H  Y  H  V  N  F  Y  S    220

ATTAGCCCGATGAGTCCGCTGAGCAAACATTTTCCGATTCCGACCGTGGAAGATGATTGT   720
 I  S  P  M  S  P  L  S  K  H  F  P  I  P  T  V  E  D  D  C    240

GAAACCACCTTTGTTGCACCGCTGAAAGAAAATTATATTAATGATATTCTGCTGCCTCCG   780
 E  T  T  F  V  A  P  L  K  E  N  Y  I  N  D  I  L  L  P  P    260

CATTTTGTGTATGAAAAACTGGGCACCATTGTGAGCAAAAAAAGCCGTTTTCATAGCAAT   840
 H  F  V  Y  E  K  L  G  T  I  V  S  K  K  S  R  F  H  S  N    280

CTGATTGTGCGTCTGATTCGTGATCTGCTGAAACTGCCGAGCGCACTGAAACATTATCTG   900
 L  I  V  R  L  I  R  D  L  L  K  L  P  S  A  L  K  H  Y  L    300

AAAGAAAAATAA                                                   912
 K  E  K                                                       303
```

FIG. 4

```
PmST3  : -------------------------- DKFAEHEIP-- AVIVAGNGESLSQIDYRLLP   :  33
CstI   : ---------------------MTRTR ENELIVSKN-MQNIIIAGNGPSL NINYKRLP E :  39
CstII  : ------------------------------------M KVIIAGNGPSL EIDYSRLPN  :  24
Lic3B  : MPNQSINQSINQSINQSINQSINQS NQSINQSINQS PVIIAGNGTSL SIDY LLP   :  60

                 *                       *
PmST3  : YDVFRCNQFYFEE YFLGNK K VFFT GV LEQY TLYHLKR  EYFVD V LS F HP :  93
CstI   : YDVFRCNQFYFE  YYLG K K VFF  GV LQQYHTAKQL LK EY IK IFCS F LP :  99
CstII  : FDVFRCNQFYFE  YYLG KCK VFY  IL FEQY TLKHL Q QEY TELI CSNY QA :  84
Lic3B  : YDVFRCNQFYFE HYFLG K KKVFF CSVIFEQY TFMQL K  EY YA I LS FLNL : 120

                                                  *  *
PmST3  : -TVDLEKSQKIQAL I VING EK  SKLTAF V   YKELYENQRITSGVYMCAVA AM : 152
CstI   : FIESNDF HQFYNF  AK G E-V ENL EFY   YNEIYFNKRITSGVYMCAIA AL : 158
CstII  : HLENENF KTFYDY  AH G D- FKQL DF  F FHEIYFNQRITSGVYMCAVA AL : 143
Lic3B  : GDSELKK QRLEKLL QID GHS- KFL AF H QYHELYENKRITSGVYMCAVATAM : 179

                     *      *                 *
PmST3  : GYTDIYL GIDFYQASEENY FDNKKPNI  LLPD KE LFSYHS DIDLEALS L Q : 212
CstI   : GY TIYLCGIDFYE-GDVIYPFEAMSTNIKTIFPGI DF PSN-CHS EYDIEALKLLKS : 216
CstII  : GY EIYL GIDFYQ-NGSSY FDTKQKNL  LAPN NDN HYIGHS NTDIKALE L K : 202
Lic3B  : GY DLYL GIDFYQEKGNPY FHHQKENI  LLPS SQN  QNDIHSMEYDLNALY L K : 239

PmST3  : HYHV FYSIS MSPLSKH  IPTVEDDCETTF APLKEN- INDILL PHFV E  GT-I : 270
CstI   : IYKV  YALCDDSILA H  LSININ---NNFTL NKHNNSINDILLTDN--TPG S--- : 268
CstII  : TYKIK YCLC NSLLA FIELAPNLN---SNF I EKNN- TKDILI SSEA G FSKNI : 258
Lic3B  : HYGV  YCIS ESPLC Y  LSPLNN--PFTF P EKKN- TQDILI PESV K  G--- : 293

PmST3  : VS  S FHSN  V   RDLL   SAL H   E ------ : 303
CstI   : F  NQLKADNK MLNFYNILHSKD LIK  NK------- : 300
CstII  : N   I IKEN YY   KDLL   S I H F G ------ : 291
Lic3B  : I S P IYQN  F   WDIL   N I KA  A KMRLRK : 332
```

PMST3 ENZYME FOR CHEMOENZYMATIC SYNTHESIS OF ALPHA-2-3-SIALOSIDES

CROSS-REFERENCES TO RELATED APPLICATIONS

This application is the U.S. National Stage Entry under §371 of International Application No. PCT/US2012/063826, filed Nov. 7, 2012, which claims priority to U.S. Provisional Application No. 61/556,620, filed Nov. 7, 2011, and U.S. Provisional Application No. 61/585,381, filed Jan. 11, 2012, which are incorporated in their entirety herein for all purposes.

STATEMENT AS TO RIGHTS TO INVENTIONS MADE UNDER FEDERALLY SPONSORED RESEARCH AND DEVELOPMENT

This invention was made with Government support under Grant No. CHE1012511, awarded by the National Science Foundation, and Grant No. R01HD065122, awarded by the National Institutes of Health. The Government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-2109-1.TXT, created on May 2, 2014, 57,344 bytes, machine format IBM-PC, MS-Windows operating system, is hereby incorporated by reference in its entirety for all purposes.

BACKGROUND OF THE INVENTION

Glycosyltransferase-catalyzed reactions have gained increasing attention and application for the synthesis of complex carbohydrates and glycoconjugates. Sialyltransferases, in particular, are the key enzymes that catalyze the transfer of a sialic acid residue from cytidine 5'-monophosphate-sialic acid (CMP-sialic acid) to an acceptor. Resulting sialic acid-containing products have been implicated in various biological and pathological processes, including cell-cell recognition, cell growth and differentiation, cancer metastasis, immunological regulation, as well as bacterial and viral infection. Besides being prevalent in mammals, sialyltransferases have been found in some pathogenic bacteria. They are mainly involved in the formation of sialic acid-containing capsular polysaccharides (CPS) and lipooligo(poly)saccharides (LOS/LPS), serving as virulence factors, preventing recognition by host's immune system, and modulating interactions with the environment. Sialyltransferases have been used for the synthesis of sialic acid-containing molecules with or without CMP-sialic acid biosynthetic enzymes (Li, Y. and Chen, X. 2012).

Cloning of sialyltransferases from various sources, including mammalian organs, bacteria, and viruses has been reported. Bacterial sialyltransferases have been cloned from several gram-negative bacteria belonging to *Escherichia, Campylobacter, Neisseria, Photobacterium, Haemophilus*, and *Pasteurella genera*. The genera *Pasteurella* and *Haemophilus*, both belong to the *Haemophilus-Actinobacillus-Pasteurella* (HAP) group, generally produced negatively charged outer cell surface and contain multiple genes encoding functional sialyltransferases. Two functional α2-3-sialyltransferases encoded by 1st and Hd0053 have been identified from *Haemophilus ducreyi*. Lic3A, SiaA, LsgB, and Lic3B are four sialyltransferases involved in the complex process of lipopolysaccharide sialylation in *Haemophilus influenzae*. Recently, a second sialyltransferase (PmST2) encoded by a Pm0508 gene homolog was characterized following the report on the first sialyltransferase from *Pasteurella multocida* encoded by a Pm0188 gene homolog (PmST1).

Most mammalian glycosyltransferases—including sialyltransferases—suffer from no or low expression in *E. coli* systems and more restricted substrate specificity. In comparison, bacterial glycosyltransferases are generally easier to access using *E. coli* expression systems and have more promiscuous substrate flexibility. Although certain wild-type bacterial glycosyltransferases with promiscuities for both donor and acceptor substrates have been discovered, readily obtainable enzymes with a wider substrate tolerance are needed to further the application of glycosyltransferases. The present invention meets this and other needs, providing surprisingly useful sialyltransferases for synthesis of glycoconjugates.

BRIEF SUMMARY OF THE INVENTION

In a first aspect, the invention provides a method of preparing a glycosylated molecule. The method includes forming a reaction mixture containing an acceptor molecule, a donor substrate having a sugar moiety and a nucleotide, and a sialyltransferase selected from PmST3 (SEQ ID NO:7) and certain variants thereof. The reaction mixture is formed under conditions sufficient to transfer the sugar moiety from the donor substrate to the acceptor molecule, thereby forming the glycosylated molecule. In some embodiments, the acceptor molecule is selected from a natural product, an oligosaccharide, a glycoprotein, and a glycolipid. In some embodiments, the donor substrate is formed via conversion of a suitable hexosamine derivative to a cytidine 5'-monophosphate(CMP)-sialic acid in a one-pot reaction mixture containing a sialic acid aldolase and a CMP-sialic acid synthetase.

In a second aspect, the invention provides an isolated or purified polynucleotide comprising a nucleotide sequence that is substantially identical to SEQ ID NO:1 (PmST3) or certain variants thereof.

In a third aspect, the invention provides an isolated or purified polypeptide comprising an amino acid sequence selected from SEQ ID NO:7 (PmST3) and certain variants thereof.

BRIEF DESCRIPTION OF THE DRAWINGS

FIG. 2A shows the alignment of DNA sequences for *Pasteurella multocida* strains Pm70 (SEQ ID NO:22), P-1059 (SEQ ID NO:23) and P-934 (SEQ ID NO:24). Underlined sequences indicate primers used to clone the gene into pET22b(+) vector. Non-coding sequences are shown in italics. Identical bases are shown as asterisks. Missing bases are shown in dashes.

FIG. 2B shows the alignment (part 2 of 2) of DNA sequences for *Pasteurella multocida* strains Pm70, P-1059 and P-934. Underlined sequences indicate primers used to clone the gene into pET22b(+) vector. Non-coding sequences are shown in italics. Identical bases are shown as asterisks. Missing bases are shown in dashes.

FIG. 3 shows the DNA (SEQ ID NO:1) and polypeptide (SEQ ID NO:7) sequences of the full length codon-optimized PmST3.

FIG. 4 shows the amino acid sequence alignment of PmST3 (SEQ ID NO:7), CstII from *Campylobacter jejuni* (SEQ ID NO:26), amino acids 1-300 of CstI from *Campylobacter jejuni* (SEQ ID NO:25), and Lic3B from *Haemophilus influenza* (SEQ ID NO:27). Black boxes indicate identical or similar amino acid residues shared by all four sequences, while grey boxes indicate identical or similar amino acid residues shared by two or three of four sequences. Amino acids with asterisks (*) indicate catalytically important amino acid residues conserved in CstI and CstII.

DETAILED DESCRIPTION OF THE INVENTION

I. General

Figure 1:
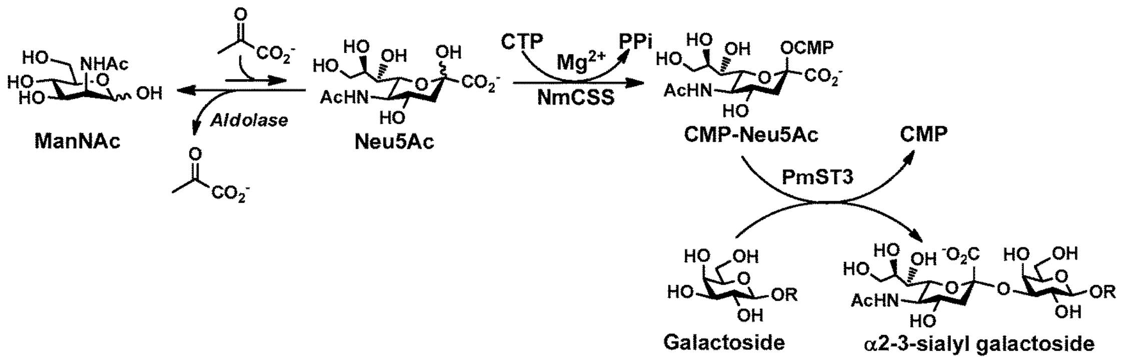
FIG. 1 shows a scheme for the one-pot, three-enzyme synthesis of α2-3-sialyl galactosides, including the sialylation of galactosides with cytidine-5'-monophosphate N-acetylneuraminic acid by PmST3.
Figure 5:
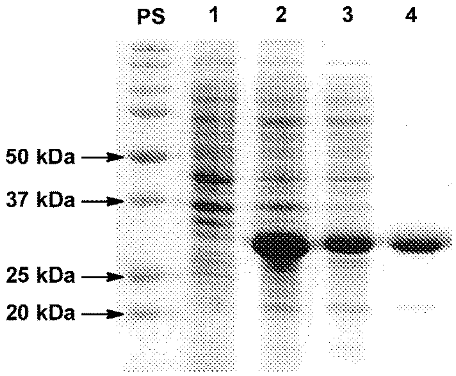
FIG. 5 shows the SDS-PAGE analysis of the expression and purification of PmST3Δ35-$His_6$. Lanes: PS, protein standards (Bio-Rad Precision Plus Protein Standards, 10-250 kDa); 1, whole cell extract before induction; 2, whole cell extract after induction; 3, lysate after induction; and 4, $Ni^{2+}$-NTA column purified protein.

The present invention provides alpha2-3 sialyltransferases useful for the preparation of glycosylated molecules. In particular, the third sialyltransferase from *Pasteurella multocida* (PmST3; encoded by gene Pm1174) is a sialidase-free monofunctional α2-3-sialyltransferase. Certain variants of soluble, active PmST3 can be obtained in high yield, making this enzyme desirable for large-scale synthesis of glycosylated products. The surprising substrate promiscuity of PmST3 is particularly advantageous, allowing for the preparation of a variety of sialic acid-containing molecules including oligosaccharides, glycopeptides, glycoproteins, and glycolipids.

II. Definitions

"Glycosyltransferase" refers to a polypeptide that catalyzes the formation of a glycoside or an oligosaccharide from a donor substrate and an acceptor or acceptor sugar. In general, a glycosyltransferase catalyzes the transfer of the monosaccharide moiety of the donor substrate to a hydroxyl group of the acceptor. The covalent linkage between the monosaccharide and the acceptor sugar can be a 1-4 linkage, a 1-3 linkage, a 1-6-linkage, a 1-2 linkage, a 2-3-linkage, a 2-4-linkage, a 2-6-linkage, a 2-8-linkage, or a 2-9-linkage. The linkage may be in the α- or β-configuration with respect to the anomeric carbon of the monosaccharide. Other types of linkages may be formed by the glycosyltransferases in the methods of the invention. Glycosyltransferases include, but are not limited to, sialyltransferases, heparosan synthases (HSs), glucosaminyltransferases, N-acetylglucosaminyltransferases, glucosyltransferases, glucuronyltransferases, N-acetylgalactosaminyltransferases, galactosyltransferases, galacturonyltransferases, fucosyltransferases, mannosyltransferases, xylosyltransferases. Sialyltransferases are enzymes that catalyze the transfer of sialic acid, or analogs thereof, to a monosaccharide, an oligosaccharide, or a glyconjugate. In some embodiments, the glycosyltransferases useful in the present invention include those in Glycosyltransferase family 80 (GT80 using CAZy nomenclature), and includes beta-galactoside alpha-2,3-sialyltransferases that catalyze the following conversion: CMP-sialic acid +β-D-galactosyl-R=CMP+α-sialic acid-(2→3)-β-D-galactosyl-R, where the acceptor is GalβOR, where R is H, a monosaccharide, an oligosaccharide, a polysaccharide, a glycopeptide, a glycoprotein, a glycolipid, or a hydroxyl-containing compound. GT80 family sialyltransferases also include galactoside or N-acetylgalactosaminide alpha-2,6-sialyltransferases that catalyze the following conversion: CMP-sialic acid+galactosyl/GalNAc-R=CMP+α-sialic acid-(2→6)-β-D-galactosyl/GalNAc-R, where the acceptor is GalOR or GalNAcOR, where R is H, serine or threonine on a peptide or protein, a monosaccharide, an oligosaccharide, a polysaccharide, a glycopeptide, a glycoprotein, a glycolipid, or a hydroxyl-containing compound.

"Sialidase" refers to an enzyme that catalyzes the hydrolysis of glycosidic linkages of terminal sialic acids on glycosylated molecules.

"Donor substrate hydrolysis" refers to hydrolysis of O-glycosidic bond of the sugar and the phosphate in the nucleotide-sugar donor substrate.

"Amino acid" refers to any monomeric unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., *Biochemistry*, $5^{th}$ ed., Freeman and Company (2002), which is incorporated by reference. Additional amino acids, such as selenocysteine and pyrrolysine, can also be genetically coded for (Stadtman (1996) "Selenocysteine," *Annu Rev Biochem.* 65:83-100 and Ibba et al. (2002) "Genetic code: introducing pyrrolysine," *Curr Biol.* 12(13):R464-R466, which are both incorporated by reference). The term "amino acid" also includes unnatural amino acids, modified amino acids (e.g., having modified side chains and/or backbones), and amino acid analogs.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-natural amino acid polymers. As used herein, the terms encompass amino acid chains of any length, including full-length proteins, wherein the amino acid residues are linked by covalent peptide bonds.

"Mutant," in the context of glycosyltransferases of the present invention, means a polypeptide, typically recombinant, that comprises one or more amino acid substitutions relative to a corresponding, naturally-occurring or unmodified glycosyltransferase, such as an alpha2-3 sialyltransferase.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

"Percent sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

"Identical" or "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% identity over a specified region), when compared and aligned for maximum correspondence over a comparison window, or designated region as measured using one of the following sequence comparison algorithms or by manual alignment and visual inspection. These definitions also refer to the complement of a test sequence. Optionally, the identity exists over a region that is at least about 50 nucleotides in length, or more typically over a region that is 100 to 500 or 1000 or more nucleotides in length.

"Similarity" or "percent similarity," in the context of two or more polypeptide sequences, refer to two or more sequences or subsequences that have a specified percentage of amino acid residues that are either the same or similar as defined by a conservative amino acid substitutions (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, at least 50%, or at least 55% similar to each other. Optionally, this similarly exists over a region that is at least about 50 amino acids in length, or more typically over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Algorithms suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

"Recombinant," as used herein, refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases, in a form not normally found in nature. Thus an isolated, mutant glycosyltransferase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" is a protein made using recombinant techniques, i.e., through the expression of a recombinant nucleic acid as depicted above.

"Vector" refers to a piece of DNA, typically double-stranded, which may have inserted into it a piece of foreign DNA. The vector may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

"Nucleotide," in addition to referring to the naturally occurring ribonucleotide or deoxyribonucleotide monomers, shall herein be understood to refer to related structural variants thereof, including derivatives and analogs, that are functionally equivalent with respect to the particular context in which the nucleotide is being used (e.g., hybridization to a complementary base), unless the context clearly indicates otherwise.

"Nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (*Science* 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

"Donor substrate" refers to a compound having a nucleotide and the sugar that is added to the acceptor, where the sugar and nucleotide are covalently bound together. The sugar can be sialic acid or analogs thereof. The nucleotide can be any suitable nucleotide such as cytidine monophosphate (CMP).

"Acceptor molecule" refers to a molecule containing a sugar that accepts the sugar being added. For example, the acceptor molecule can be an oligosaccharide, such as a fucosylated oligosaccharide, that accepts a sialic acid or analog thereof.

"Oligosaccharide" refers to a compound containing at least two sugars covalently linked together. Oligosaccharides include disaccharides, trisaccharides, tetrasachharides, pentasaccharides, hexasaccharides, heptasaccharides, octasaccharides, and the like. Covalent linkages for linking sugars generally consist of glycosidic linkages (i.e., C—O—C bonds) formed from the hydroxyl groups of adjacent sugars. Linkages can occur between the 1-carbon (the anomeric carbon) and the 4-carbon of adjacent sugars (i.e., a 1-4 linkage), the 1-carbon (the anomeric carbon) and the 3-carbon of adjacent sugars (i.e., a 1-3 linkage), the 1-carbon (the anomeric carbon) and the 6-carbon of adjacent sugars (i.e., a 1-6 linkage), or the 1-carbon (the anomeric carbon) and the 2-carbon of adjacent sugars (i.e., a 1-2 linkage). A sugar can be linked within an oligosaccharide such that the anomeric carbon is in the α- or β-configuration. The oligosaccharides prepared according to the methods of the invention can also include linkages between carbon atoms other than the 1-, 2-, 3-, 4-, and 6-carbons.

"Natural product" refers to a chemical compound that is produced (or can be produced) by a living organism. Natural products used in the methods of the present invention generally include a sugar moiety or an oligosaccharide moiety. Examples of natural products include, but are not limited to, non-ribosomal glycopeptides, glycoalkaloids, ginsenosides, aminoglycosides, avermectins, and anthracyclines.

"Glycolipid" refers to a lipid containing a sugar moiety or an oligosaccharide moiety. Examples of glycolipids include, but are not limited to, glycoglycerolipids, glycosphingolipids, glycosyl polyisoprenol pyrophosphates, and glycophosphatidylinositols.

"Glycoprotein" and "glycopeptide" refer to a polypeptide or oligopeptide, respectively, containing a sugar moiety or an oligosaccharide moiety. Examples of glycoproteins include, but are not limited to, mucins, immunoglobulins, selectins, and collagens.

"CMP-sialic acid synthetase" refers to a polypeptide that catalyzes the synthesis of cytidine monophosphate sialic acid (CMP-sialic acid) from cytidine triphosphate (CTP) and sialic acid.

"Sialic acid aldolase" refers to an aldolase that catalyzes a reversible reaction that converts a suitable hexosamine, hexose, pentose, or derivative (such as N-acetyl mannosamine) to sialic acid via reaction with pyruvate.

III. Sialyltransferases

Sialyltransferases are one class of glycosyltransferases, enzymes that catalyze the transfer of a sugar from a nucleotide-sugar (donor substrate) to an acceptor (e.g., a natural prodruct, a monosaccharide, an oligosaccharide, a glycolipid, a glycoprotein, or a hydroxyl-containing compounds). Specifically, sialyltransferases catalyze the transfer of sialic acid, or analogs thereof, from a sialic acid-nucleotide donor substrate to the terminal sugar of an acceptor substrate. Representative sialyltransferases include, but are not limited to, sialyltransferases in family EC 2.4.99, such as beta-galactosamide alpha-2,6-sialyltransferase (EC 2.4.99.1), alpha-N-acetylgalactosaminide alpha-2,6-sialyltransferase (EC 2.4.99.3), beta-galactoside alpha-2,3-sialyltransferase (EC 2.4.99.4), N-acetyllactosaminide alpha-2,3-sialyltransferase (EC 2.4.99.6), alpha-N-acetyl-neuraminide alpha-2,8-sialyltransferase (EC 2.4.99.8), and lactosylceramide alpha-2,3-sialyltransferase (EC 2.4.99.9). The sialyltransferases of the present invention also include those of the CAZy GT80 family, or EC 2.4.99.4 and EC 2.4.99.1, made up of alpha2-3 and alpha2-6 sialyltransferases, as well as sialyltransferases in the GT4, GT29, GT30, GT38, GT42, GT52, and GT73 families. Representative GT80 sialyltransferases include, but are not limited to, PmST1, Psp26ST, Vsp23ST, Pd26ST, P1ST6 JT-1, P1ST6 JT-2, Pp Pst3-1, Pp Pst3-2, Np23ST and Hd0053. (See Glycobiology 2011, 21(6), 716; J. Mol. Biol. 2003, 328, 307; Annu. Rev. Biochem. 2008, 77, 521; Appl. Microbiol. Biotechnol. 2012, 94, 887 for review of sialyltransferases.) PmST3 is a preferred sialyltransferase in some embodiments of the invention.

In general, the sialyltransferases of the present invention are α2-3-sialyltransferases. The α2-3-sialyltransferases of the present invention can include sialyltransferases of *Pasteurella multocida*. The sialyltransferases include those having decreased α2-3 sialidase activity compared to a control glycosyltransferase. For certain sialyltransferases of the invention, this activity is essentially absent. α2-3 sialidase activity, in particular, refers to the cleavage of the glycosidic bond between the sialic acid from the donor substrate and the sugar of the acceptor molecule, which results in free sialic acid and the acceptor.

The sialyltransferases of the present invention can include a polypeptide having any suitable percent identity to a reference sequence (e.g., SEQ ID NO: 7). For example, the glycosyltransferases of the present invention can include a polypeptide having a percent sequence identity to the control glycosyltransferase sequence of at least 20, 30, 40, 50, 55, 60, 65, 70, 75, 80, 85, 90, 91, 92, 93, 94, 95, 96, 97, 98 or at least 99%. In some embodiments, percent sequence identity can be at least 80%. In some embodiments, percent sequence identity can be at least 90%. In some embodiments, percent sequence identity can be at least 95%.

In some embodiments, the invention provides an isolated or purified polypeptide including an amino acid sequence selected from SEQ ID NO: 7 (PmST3); SEQ ID NO: 8 (PmST3-$His_6$); SEQ ID NO: 9 (MBP-PmST3-$His_6$); SEQ ID NO: 10 (PmST3Δ20-$His_6$); SEQ ID NO: 11 (PmST3Δ35-$His_6$); and SEQ ID NO: 12 (PmST3Δ45-$His_6$). In some embodiments, the polypeptide comprises an amino acid sequence selected from SEQ ID NO:13 (sialyltransferase motif A), SEQ ID NO:14 (sialyltransferase motif B), and SEQ ID NO:15 (sialyltransferse motif C).

The precise length of the sialyltransferases can vary, and certain variants can be advantageous for expression and purification of the enzymes in high yield. For example, removal of certain peptide subunits from the overall polypeptide sequence of a sialyltransferase can improve solubility of the enzyme and increase expression levels. Alternatively, addition of certain peptide or protein subunits to a sialyltransferase polypeptide sequence can modulate expression, solubility, activity, or other properties. The sialyltransferases of the present invention can include point mutations at any position of the PmST3 wild type sequence or a PmST3 variant (e.g., a fusion protein or a truncated form). The mutants can include any suitable amino acid other than the native amino acid. For example, the amino acid can be V, I, L, M, F, W, P, S, T, A, G, C, Y, N, Q, D, E, K, R, or H. Amino acid and nucleic acid sequence alignment programs are readily available (see, e.g., those referred to supra) and, given the particular motifs identified herein, serve to assist in the identification of the exact amino acids (and corresponding codons) for modification in accordance with the present invention.

The sialyltransferases of the present invention can be constructed by mutating the DNA sequences that encode the corresponding unmodified sialyltransferase (e.g., a wild-type sialyltransferase or a corresponding variant), such as by using techniques commonly referred to as site-directed mutagenesis. Nucleic acid molecules encoding the unmodified form of the sialyltransferase can be mutated by a variety of techniques well-known to one of ordinary skill in the art. (See, e.g., *PCR Strategies* (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, NY, 1990).

By way of non-limiting example, the two primer system, utilized in the Transformer Site-Directed Mutagenesis kit from Clontech, may be employed for introducing site-directed mutants into a polynucleotide encoding an unmodified form of the sialyltransferase. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids result in high mutation efficiency and allow minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Mutagenesis can also be conducted using a QuikChange multisite-directed mutagenesis kit (Stratagene) and the like. Transformants can be screened by sequencing the plasmid DNA through the mutagenized region to identify and sort mutant clones. Each mutant DNA can then be restricted and analyzed by electrophoresis, such as for example, on a Mutation Detection Enhancement gel (Mallinckrodt Baker, Inc., Phillipsburg, N.J.) to confirm that no other alterations in the sequence have occurred (by band shift comparison to the unmutagenized control). Alternatively, the entire DNA region can be sequenced to confirm that no additional mutational events have occurred outside of the targeted region.

Verified mutant duplexes in pET (or other) overexpression vectors can be employed to transform *E. coli* such as, e.g., strain *E. coli* BL21 (DE3) or strain *E. coli* BL21 (DE3) pLysS, for high level production of the mutant protein, and purification by standard protocols. The method of FAB-MS mapping, for example, can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutated protein). The set of cleavage fragments is fractionated by, for example, HPLC (reversed phase or ion exchange, again depending on the specific region to be modified) to provide several peptides in each fraction, and the molecular weights of the peptides are determined by standard methods, such as FAB-MS. The determined mass of each fragment are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS data agrees with prediction. If necessary to verify a changed residue, CAD-tandem MS/MS can be employed to sequence the peptides of the mixture in question, or the target peptide can be purified for subtractive Edman degradation or carboxypeptidase Y digestion depending on the location of the modification.

Recombinant Nucleic Acids

Sialyltransferase variants can be generated in various ways. In the case of amino acids located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: DNA encoding the unmodified sialyltransferase is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on. Alternatively, the multi-site mutagenesis method of Seyfang & Jin (*Anal. Biochem.* 324:285-291. 2004) may be utilized.

Accordingly, also provided are recombinant nucleic acids, optionally isolated, encoding any of the sialyltransferases of the present invention. In some embodiments, the invention provides an isolated or purified polynucleotide including a nucleotide sequence that is substantially identical to a sequence selected from SEQ ID NO:1 (PmST3), SEQ ID NO:2 (PmST3-$His_6$), SEQ ID NO:3 (MBP-PmST3-$His_6$), SEQ ID NO:4 (PmST3Δ20-$His_6$), SEQ ID NO:5 (PmST3Δ35-$His_6$), SEQ ID NO:6 (PmST3Δ45-$His_6$), SEQ ID NO:16 (WTPmST3), SEQ ID NO:17 (WTPmST3-$His_6$), SEQ ID NO:18 (MBP-WTPmST3-$His_6$), SEQ ID NO:19 (WTPmST3Δ20-$His_6$), SEQ ID NO:20 (WTPmST3Δ35-$His_6$), and SEQ ID NO:21 (WTPmST3Δ45-$His_6$), or complements thereof. In some embodiments, the polynucleotide includes a nucleotide sequence that is substantially identical to a sequence selected from SEQ ID NO:1 (PmST3), SEQ ID NO:2 (PmST3-$His_6$), SEQ ID NO:3 (MBP-PmST3-$His_6$), SEQ ID NO:4 (PmST3Δ20-$His_6$), SEQ ID NO:5 (PmST3Δ35-$His_6$), and SEQ ID NO:6 (PmST3Δ45-$His_6$), or complements thereof. In some embodiments, the polynucleotide comprises a polynucleotide sequence encoding SEQ ID NO:13 (sialyltransferase motif A), SEQ ID NO:14 (sialyltransferase motif B), or SEQ ID NO:15 (sialyltransferse motif C), or the complement of a sequence that encodes SEQ ID NO:13, 14, or 15. In general, the polynucleotide has at least 50% sequence identity to a sequence selected from SEQ ID NOS: 1, 2, 3, 4, 5, 6, 16, 17, 18, 19, 20, 21, and complements thereof. In some embodiments, the polynucleotide has at least 50% sequence identity to a sequence selected from SEQ ID NOS: 1, 2, 3, 4, 5, 6, and complements thereof. The sequence identity can be, for example, 50%, 55%, 60%, 65%, 70%, 75%, 80%, 85%, 90%, 91%, 92%, 93%, 94%, 95%, 96%, 97%, 98%, 99%, or 100%. In some embodiments, a given polynucleotide can be optimized for expression in yeast. In some embodiments, the polynucleotide contains a sequence selected from SEQ ID NOS: 1, 2, 3, 4, 5, 6, 16, 17, 18, 19, 20, 21, and complements thereof. In some embodiments, the polynucleotide contains a sequence selected from SEQ ID NOS: 1, 2, 3, 4, 5, 6, and complements thereof.

Using a nucleic acid of the present invention, encoding a sialyltransferase of the invention, a variety of vectors can be made. Any vector containing replicon and control sequences that are derived from a species compatible with the host cell can be used in the practice of the invention. Generally, expression vectors include transcriptional and translational regulatory nucleic acid regions operably linked to the nucleic acid encoding the mutant sialyltransferase. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. In addition, the vector may contain a Positive Retroregulatory Element (PRE) to enhance the half-life of the transcribed mRNA (see Gelfand et al. U.S. Pat. No. 4,666,848). The transcriptional and translational regulatory nucleic acid regions will generally be appropriate to the host cell used to express the sialyltransferase. Numerous types of appropriate expression vectors, and suitable regulatory sequences are known in the art for a variety of host cells. In general, the transcriptional and translational regulatory sequences may include, e.g., promoter sequences, ribosomal binding sites, transcriptional start and stop sequences, translational start and stop sequences, and enhancer or activator sequences. In typical embodiments, the regulatory sequences include a promoter and transcriptional start and stop sequences. Vectors also typically include a polylinker region containing several restriction sites for insertion of foreign DNA. In certain embodiments, "fusion flags" are used to facilitate purification and, if desired, subsequent removal of tag/flag sequence, e.g., "His-Tag". However, these are generally unnecessary when purifying an thermoactive and/or thermostable protein from a mesophilic host (e.g., *E. coli*) where a "heat-step" may be employed. The construction of suitable vectors containing DNA encoding replication sequences, regulatory sequences, phenotypic selection genes, and the mutant sialyltransferase of interest are prepared using standard recombinant DNA procedures. Isolated plasmids, viral vectors, and DNA fragments are cleaved, tailored, and ligated together in a specific order to generate the desired vectors, as is well-known in the art (see, e.g., Sambrook et al., *Molecular Cloning: A Laboratory Manual* (Cold Spring Harbor Laboratory Press, New York, N.Y., 2nd ed. 1989)). In some embodiments, the present invention provides a recombinant nucleic acid encoding an isolated sialyltransferase of the present invention.

Host Cells

In certain embodiments, the expression vector contains a selectable marker gene to allow the selection of transformed host cells. Selection genes are well known in the art and will vary with the host cell used. Suitable selection genes can include, for example, genes coding for ampicillin and/or tetracycline resistance, which enables cells transformed with these vectors to grow in the presence of these antibiotics.

In one aspect of the present invention, a nucleic acid encoding a sialyltransferase of the invention is introduced into a cell, either alone or in combination with a vector. By "introduced into" or grammatical equivalents herein is meant that the nucleic acids enter the cells in a manner suitable for subsequent integration, amplification, and/or expression of the nucleic acid. The method of introduction is largely dictated by the targeted cell type. Exemplary methods include $CaPO_4$ precipitation, liposome fusion, LIPOFECTIN®, electroporation, viral infection, and the like.

In some embodiments, prokaryotes are used as host cells for the initial cloning steps of the present invention. Other host cells include, but are not limited to, eukaryotic (e.g., mammalian, plant and insect cells), or prokaryotic (bacterial) cells. Exemplary host cells include, but are not limited to, *Escherichia coli, Saccharomyces cerevisiae, Pichia pastoris*, Sf9 insect cells, and CHO cells. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3110 (ATCC No. 27,325), *E. coli* K12 strain DG116 (ATCC No. 53,606), *E. coli* X1776 (ATCC No. 31,537), and *E. coli* B; however many other strains of *E. coli*, such as HB 101, JM101, NM522, NM538, NM539, and many other species and genera of prokaryotes including bacilli such as *Bacillus subtilis*, other enterobacteriaceae such as *Salmonella typhimurium* or *Serratia marcesans*, and various *Pseudomonas* species can all be used as hosts. Prokaryotic host cells or other host cells with rigid cell walls are typically transformed using the calcium chloride method as described in section 1.82 of Sambrook et al., supra. Alternatively, electroporation can be used for transformation of these cells. Prokaryote transformation techniques are set forth in, for example Dower, in *Genetic Engineering, Principles and Methods* 12:275-296 (Plenum Publishing Corp., 1990); Hanahan et al., *Meth. Enzymol.,* 204:63, 1991. Plasmids typically used for transformation of *E. coli* include pBR322, pUCI8, pUCI9, pUCI18, pUC119, and Bluescript M13, all of which are described in sections 1.12-1.20 of Sambrook et al., supra. However, many other suitable vectors are available as well.

In some embodiments, the sialyltransferases of the present invention are produced by culturing a host cell transformed with an expression vector containing a nucleic acid encoding the sialyltransferase, under the appropriate conditions to induce or cause expression of the sialyltransferase. Methods of culturing transformed host cells under conditions suitable for protein expression are well-known in the art (see, e.g., Sambrook et al., supra). Suitable host cells for production of the sialyltransferases from lambda pL promoter-containing plasmid vectors include *E. coli* strain DG116 (ATCC No. 53606) (see U.S. Pat. No. 5,079,352 and Lawyer, F. C. et al., *PCR Methods and Applications* 2:275-87, 1993, which are both incorporated herein by reference). Following expression, the sialyltransferase can be harvested and isolated. Methods for purifying thermostable glycosyltransferases are described in, for example, Lawyer et al., supra. In some embodiments, the present invention provides a cell including a recombinant nucleic acid of the present invention. In some embodiments, the cell can be prokaryotes, eukaryotes, mammalian, plant, bacteria or insect cells.

IV. Methods of Making Oligosaccharides

The sialyltransferases of the present invention can be used to prepare oligosaccharides, specifically to add N-acetylneuraminic acid (Neu5Ac), other sialic acids, and analogs thereof, to a monosaccharide, an oligosaccharide, a glycolipid, a glycopeptide, or a glycoprotein. As shown in FIG. 1, for example, PmST3 catalyzes the addition of CMP-Neu5Ac to a fucosylated oligosaccharide by transferring the Neu5Ac to the oligosaccharide.

Accordingly, some embodiments of the present invention provide a method of preparing a glycosylated molecule. The method includes forming a reaction mixture containing an acceptor molecule, a donor substrate having a sugar moiety and a nucleotide, and a glycosyltransferase of the present invention. The glycosyltransferase includes a polypeptide having a sequence that is substantially identical to a sequence selected from SEQ ID NO:7 (PmST3), SEQ ID NO:8 (PmST3-$His_6$), SEQ ID NO:9 (MBP-PmST3-$His_6$), SEQ ID NO:10 (PmST3Δ20-$His_6$), SEQ ID NO:11 (PmST3Δ35-$His_6$), and SEQ ID NO:12 (PmST3Δ45-$His_6$). The reaction mixture is formed under conditions sufficient to transfer the sugar moiety from the donor substrate to the acceptor molecule, thereby forming the glycosylated molecule.

In some embodiments, the acceptor molecule is selected from a natural product, an oligosaccharide, a glycolipid, a glycopeptide, and a glycoprotein. Suitable natural products include non-ribosomal glycopeptides (such as bleomycin), glycoalkaloids (such as solanine), ginsenosides (such as sanchinoside C1), aminoglycosides (such as gentamicin, kanamycin, neomycin, and streptomycin), avermectins, and anthracyclines (such as daunorubicin). Suitable glycolipids include glycoglycerolipids (such as monogalactosyldiacylglycerols, digalactosylmonoacylglycerols, and sulfoquinovosyl diacylglycerols), glycosphingolipids (such as lacto-, neolacto-, ganglio-, globo-, and iso-globo-series glycosphinlolipids), and glycophosphatidylinositols (e.g., 1-phosphatidyl-L-myo-inosito 2,6-di-O-α-D-mannopyranoside.). Suitable glycoproteins include mucins, immunoglobulins, lectins, and collagens.

When the acceptor molecule is an oligosaccharide, any suitable oligosaccharide can be used. For example, the acceptor molecule can be Galβ1-4GlcNAcβOR, wherein R can be H, a sugar, or an oligosaccharide. In some embodiments, the acceptor molecule includes a galactoside moiety. In some embodiments, the galactoside moiety is selected from a β1-4 linked galactoside moiety and a β1-3 linked galactoside moiety. In some embodiments, the acceptor molecule includes a lactose moiety or an N-acetyl lactose moiety. In some embodiments, the acceptor molecule comprises a lacto-N-biose or a galacto-N-biose moiety.

The donor substrate of the present invention includes a nucleotide and sugar. Suitable nucleotides include, but are not limited to, adenine, guanine, cytosine, uracil and thymine nucleotides with one, two or three phosphate groups. In some embodiments, the nucleotide can be cytidine monophosphate (CMP). The sugar can be any suitable sugar. For example, the sugar can be N-acetylneuraminic acid (Neu5Ac) or other sialic acids and analogs thereof. Sialic acid is a general term for N- and O-substituted derivatives of neuraminic acid, and includes, but is not limited to, N-acetyl (Neu5Ac) or N-glycolyl (Neu5Gc) derivatives, as well as O-acetyl, O-lactyl, O-methyl, O-sulfate and O-phosphate derivatives. In some embodiments, the sialic acid can be a compound of the formula:

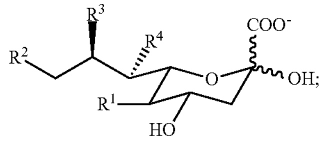

wherein $R^1$ is selected from H, OH, $N_3$, NHC(O)Me, NHC(O)$CH_2$OH, NHC(O)$CH_2N_3$, NHC(O)O$CH_2$C═$CH_2$, NHC(O)OCHC≡CH, NHC(O)$CH_2$F, NHC(O)$CH_2$NHCbz, NHC(O)$CH_2$OC(O)Me, and NHC(O)$CH_2$OBn; and $R^2$, $R^3$, and $R^4$ are independently selected from H, OH, $N_3$, OMe, F, $OSO_3^-$, $OPO_3H^-$, and OC(O)Me. In some embodiments, the donor substrate is a cytidine 5'-monophosphate(CMP)-sialic acid. In some embodiments, the CMP-sialic acid is cytidine 5'-monophosphate N-acetylneuraminic acid (CMP-Neu5Ac) or a CMP-Neu5Ac analog. Other donor substrates are useful in the methods of the present invention. In other embodiments, the sialic acid can be a compound of the formula:

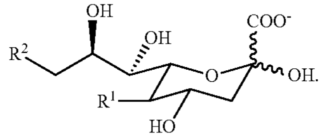

In some embodiments, the sialic acid can be a compound of the formula:

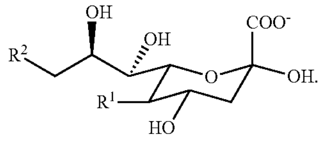

The methods of the invention include providing reaction mixtures that contain the sialyltransferases described herein. The sialyltransferases can be, for example, purified prior to addition to the reaction mixture or secreted by a cell present in the reaction mixture. Alternatively, a sialyltransferase can catalyze the reaction within a cell expressing the sialyltransferase.

Reaction mixtures can contain additional reagents for use in glycosylation techniques. For example, in certain embodiments, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, tetrahydrofuran, acetone, and acetic acid), salts (e.g., NaCl, KCl, $CaCl_2$, and salts of $Mn^{2+}$ and $Mg^{2+}$), chelators (e.g., ethylene glycol-bis(2-aminoethylether)-N,N,N',N'-tetraacetic acid (EGTA), 2-({2-[Bis(carboxymethyl)amino]ethyl}(carboxymethyl)amino)acetic acid (EDTA), and 1,2-bis(o-aminophenoxy)ethane-N,N,N',N'-tetraacetic acid (BAPTA)), reducing agents (e.g., dithiothreitol (DTT), β-mercaptoethanol (BME), and tris(2-carboxyethyl)phosphine (TCEP)), and labels (e.g., fluorophores, radiolabels, and spin labels). Buffers, cosolvents, salts, chelators, reducing agents, and labels can be used at any suitable concentration, which can be readily determined by one of skill in the art. In general, buffers, cosolvents, salts, chelators, reducing agents, and labels are included in reaction mixtures at concentrations ranging from about 1 μM to about 1 M. For example, a buffer, a cosolvent, a salt, a chelator, a reducing agent, or a label can be included in a reaction mixture at a concentration of about 1 μM, or about 10 μM, or about 100 μM, or about 1 mM, or about 10 mM, or about 25 mM, or about 50 mM, or about 100 mM, or about 250 mM, or about 500 mM, or about 1 M.

Reactions are conducted under conditions sufficient to transfer the sugar moiety from a donor substrate to an acceptor molecule. The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 6 to about 10. The reactions can be conducted, for example, at a pH of from about 6.5 to about 9. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. Other reaction conditions may be employed in the methods of the invention, depending on the identity of a particular sialyltransferase, donor substrate, or acceptor molecule.

The donor substrate can be prepared prior to preparation of the oligosaccharide, or prepared in situ immediately prior to preparation of the oligosaccharide. In some embodiments, the method of the present invention also includes forming a reaction mixture including a CMP-sialic acid synthetase, cytidine triphosphate, and N-acetylneuraminic acid (Neu5Ac) or a Neu5Ac analog, under conditions suitable to form CMP-Neu5Ac or a CMP-Neu5Ac analog. Any suitable CMP-sialic acid synthetase (i.e., N-acylneuraminate cytidylyltransferase, EC 2.7.7.43) can be used in the methods of the invention. For example, CMP-sialic acid synthetases from *E. coli, C. thermocellum, S. agalactiae*, or *N. meningitidis* can be used. In some embodiments, the step of forming the donor substrate and the step of forming the oligosaccharide are performed in one pot.

In some embodiments, the sugar moiety of the donor substrate is prepared separately prior to use in the methods of the present invention. Alternatively, the sugar moiety can be prepared in situ immediately prior to use in the methods of the present invention. In some embodiments, the method also includes forming a reaction mixture including a sialic acid aldolase, pyruvic acid or derivatives thereof, and N-acetylmannosamine or derivatives thereof, under conditions suitable to form Neu5Ac or a Neu5Ac analog. Any suitable sialic acid aldolase (i.e., N-Acetylneuraminate pyruvate lyase, EC 4.1.3.3) can be used in the methods of the invention. For example, sialic acid aldolases from *E. coli, L. plantarum, P. multocida*, or *N. meningitidis* can be used. In some embodiments, the step of forming the sugar moiety, the step of forming the donor substrate, and the step of forming the oligosaccharide are performed in one pot.

The glycosylated molecule prepared by the method of the present invention can include a variety of glycosylated natural products, oligosaccharides, glycolipids, glycoproteins, and hydroxyl-containing compounds. In some embodiments, the glycosylated molecule contains an α2-3-linked sialic acid residue. In some embodiments, the glycosylated molecule can be Neu5Acα2-3Gal βOR wherein R is selected from H, a monosaccharide, an oligosaccharide, a glycolipid, and a glycoprotein/peptide. In some embodiments, the glycosylated molecule can be Neu5Acα2-3Galβ1-4GlcNAcβOR, wherein R is selected from H, a monosaccharide, an oligosaccharide, a glycolipid, and a glycoprotein/peptide.

V. EXAMPLES

General Materials and Methods

Chemicals and Reagents

T4 DNA ligase, 1 kb DNA ladder, and BamHI restriction enzyme were from Promega (Madison, Wis.). Herculase enhanced DNA polymerase was from Stratagene (La Jolla, Calif.). DNeasy Tissue kit, QIAprep spin miniprep kit, and QIAEX II gel extraction kit were bought from Qiagen (Valencia, Calif.). Nickel-nitrilotriacetic acid ($Ni^{2+}$-NTA) agarose was obtained from Fisher Scientific (Tustin, Calif.). Precision Plus Protein Standards, Quick Start™ Bradford protein assay, and BioGel P-2 fine resin were from Bio-Rad (Hercules, Calif.). Cytidine 5'-triphosphate (CTP), N-acetylmannosamine (ManNAc), and sodium pyruvate were purchased from Sigma (St. Louis, Mo.). Cytidine 5'-monophosphate N-acetylneuraminic acid (CMP-Neu5Ac) was synthesized enzymatically from ManNAc, pyruvate (5 equiv.), and CTP using a one-pot two-enzyme system containing a recombinant sialic acid aldolase cloned from *E. coli* K12 and a recombinant *N. meningitidis* CMP-sialic acid synthetase (NmCSS) as described previously (*Bioorganic & medicinal chemistry,* 12:6427-6435). Acceptor substrates containing a methyl 2-aminobenzoate (2AA) group including LacβPro2AA, LacNAcβPro2AA, GalNAcαPro2AA, and Galβ1-3GlcNAcβPro2AA were synthesized according to a previous method (2010. Helicobacter hepaticus Hh0072 gene encodes a novel {alpha} 1-3-fucosyltransferase belonging to CAZy GT11 family. *Glycobiology*). LacβMU (4-methylumbelliferyl β-lactoside) was synthesized as reported previously (*J Am Chem Soc,* 127:17618-17619; *Bioorganic & medicinal chemistry,* 12:6427-6435) and GalβpNP (p-nitrophenyl β-galactoside) was purchased from Sigma (St. Louis, Mo.). Acceptors containing a Pro-triazole-C14 tag including LacβPro-triazole-C14, LacNAcβPro-triazole-C14, Galβ1-3GlcNAcαPro-triazole-C14, Galβ1-3GlcNAcβPro-triazole-C14, Galβ1-3GalNAcαPro-triazole-C14, and GalβPro-triazole-C14 were synthesized as described previously (*Glycobiology,* 21:1206-1216).

Bacterial Strains and Plasmids

Electrocompetent *E. coli*DH5α cells and chemically competent *E. coli* BL21(DE3) cells were from Invitrogen (Carlsbad, Calif.). *Pasteurella multocida* genomic DNAs were prepared from strains P-1059 (ATCC#15742) and P-934 [Type D] (ATCC#12948) obtained from American Type Culture Collection (ATCC, Manassas, Va.). Expression vector pMAL-c4X and restriction enzymes XhoI, EcoRI, and HindIII were purchased from New England Biolabs (Ipswich, Mass.). Expression vector pET22b(+) was purchased from Novagen/EMD Biosciences, Inc. (Madison, Wis.).

Example 1. Cloning, Expression, and Purification of PmST3

Materials and Methods

Cloning of PmST3. Synthetic gene with codons optimized for *E. coli* expression was synthesized by Biomatik Corporation (Wilmington, Del.) based on Pm1174 gene sequence from Pm strain Pm70 (GenBank accession number: AE004439). Primers used for cloning are listed in Table 1. Polymerase chain reactions (PCRs) were performed in a reaction mixture of 50 μl containing the synthetic gene as the template DNA (1 μg), forward and reverse primers (1 μM each), 10× Herculase buffer (5 μl), dNTP mixture (1 mM), and 5 U (1 μl) of Herculase-enhanced DNA polymerase. The reaction mixture was subjected to 30 cycles of amplification with an annealing temperature of 55° C. The resulting PCR products were purified, digested, and ligated with the corresponding pre-digested vector. The ligation products were transformed into electrocompetent *E. coli* DH5α cells. Plasmids containing the target genes as confirmed by DNA sequencing (performed by UC-Davis Sequencing Facility) were selected and transformed into *E. coli* BL21(DE3) chemically competent cells.

TABLE 1

Primers used for cloning of PmST3.

| Primer name | Sequence |
|---|---|
| 5'-pET22b-PmST3 | 5'-GATCCATATGGATAAATTTGCCGAACA TGAAATTC-3' (SEQ ID NO: 28) (NdeI restriction site is underlined) |

TABLE 1-continued

Primers used for cloning of PmST3.

| Primer name | Sequence |
|---|---|
| 3'-pET22b-PmST3 | 5'-CCGCTCGAGTTTTTCTTTCAGATAAT GTTTCAG-3' (SEQ ID NO: 29) (XhoI restriction site is underlined) |
| 3'-pET22b-PmST3Δ20 | 5'-CAGCGTCGACCACAATCAGATTGCTAT GAAAACGGC-3' (SEQ ID NO: 30) (SalI restriction site is underlined) |
| 3'-pET22b-PmST3Δ35 | 5'-CAGCGTCGACGCCCAGTTTTTCATACA CAAAATGCGG-3' (SEQ ID NO: 31) (SalI restriction site is underlined) |
| 3'-pET22b-PmST3Δ45 | 5'-CAGCGTCGACCAGCAGAATATCATTAA TATAATTTTC-3' (SEQ ID NO: 32) (SalI restriction site is underlined) |
| 5'-pMAL-c4X-PmST3 | 5'-GACCGAATTCATGGATAAATTTGCCGAA CATGAAATTC-3' (SEQ ID NO: 33) (EcoRI restriction site is underlined) |
| 3'-pMAL-c4X-PmST3 | 5'-GATCAAGCTTTTAGTGGTGGTGGTGGTG GTGTTTTTCTTTCAGATAATGTTTCAG-3' (SEQ ID NO: 34) (HindIII restriction site is underlined) |

PCR analysis of the absence of Pm1174 gene homolog in Pm strains P-1059 and P-934 Primers designed based on the DNA sequences of Pm1173 and Pm1175 of Pm strain Pm70 (GenBank accession number AE004439) were used to clone partial sequences of Pm1173 and Pm1175 with DNA sequence that connect these two genes into pET22b(+) vector from the genomic DNAs of Pm strains P-1059 and strain P-934 [Type D]. The primers used were: forward 5'-GATCCATATGTCACAATCGCTTCAAATAATGGGGTC-3' (SEQ ID NO:35) corresponding to internal sequence of Pm1173 gene with an NdeI restriction site (underlined and italicized); reverse 5'-CCG CTCGAGCCACGCAGCCTCAATATCATCAACAG-3' (SEQ ID NO:36) corresponding to internal sequence of Pm1175 gene with an XhoI restriction site (underlined and italicized).

Expression and Purification.

Protein overexpression was achieved by inducing the *E. coli* BL21(DE3) cell culture with 0.1 mM of isopropyl-1-thio-β-D-galactopyranoside (IPTG) when the $OD_{600\ nm}$ of the culture reached 0.8-1.0 followed by incubation at 20° C. for 18-20 h. Bacterial cells were harvested by centrifugation at 4° C. in a Sorvall Legend RT centrifuge with a hanging bucket rotor at 3,696×g for 2 h. Harvested cells were resuspended in lysis buffer (Tris-HCl buffer, 100 mM, pH 8.0 containing 0.1% Triton X-100) (20 ml for cells collected from one liter cell culture). Lysozyme (100 μg $ml^{-1}$) and DNaseI (5 μg $ml^{-1}$) were added to the cell resuspension. The resulting mixture was incubated at 37° C. for 1 h with shaking at 210 rpm. Cell lysate (supernatant) was obtained by centrifugation at 14,905×g for 45 min. Purification was carried out by loading the supernatant onto a $Ni^{2+}$-NTA column pre-equilibrated with 10 column volumes of binding buffer (10 mM imidazole, 0.5 M NaCl, (50 mM Tris-HCl, pH 7.5). The column was washed with 10 column volumes of binding buffer and 10 column volumes of washing buffer (50 mM imidazole, 0.5 M NaCl, 50 mM Tris-HCl, pH 7.5). The target protein was eluted with Tris-HCl buffer (50 mM, pH 7.5) containing imidazole (200 mM) and NaCl (0.5 M). The fractions containing the purified enzymes were collected and dialyzed against Tris-HCl buffer (20 mM, pH 7.5) containing 10% glycerol. Dialyzed proteins were stored at 4° C.

Sodium Dodecylsulfate-Polyacrylamide Gel Electrophoresis (SDS-PAGE).

SDS-PAGE was performed in 12% Tris-glycine gels using Bio-Rad Mini-protein III cell gel electrophoresis unit (Bio-Rad, Hercules, Calif.) at DC=150 V. Bio-Rad Precision Plus Protein Standards (10-250 kDa) were used as molecular weight standards. Gels were stained with Coomassie Blue.

Quantification of Purified Protein.

Protein concentration was determined in a 96-well plate using Quick Start™ Bradford protein assay Kit (Bio-Rad, Hercules, Calif.) with bovine serum albumin as a protein standard. The absorbance of each sample was measured at 595 nm on a multiple-well plate reader (BioTek Synergy HT RDR Multidetection Plate Reader).

Results

The Pm1174 gene in Pm strain Pm70 is absent in Pm strains P-1059 and P-934. Sialyltransferases PmST1 and PmST2 encoded by Pm0188 and Pm0508 gene homologs, respectively, have been cloned and characterized from Pm strain P-1059. However, attempts to clone a homolog of Pm1174 gene from the same P-1059 strain and another Pm strain P-934 were failed. To confirm whether the Pm1174 gene homolog is missing from these two strains, PCR was carried out using the genomic DNAs of Pm strain P-934 and P-1059 as templates and primers designed based on the internal sequences of Pm1173 and Pm1175 genes in Pm strain Pm70. Indeed, PCR products of about 1.1 kbp instead of the predicted 2.0 kbp from Pm70 genomic DNA sequence were obtained. Cloning of the PCR products to pET22b(+) vector followed by DNA sequencing confirmed the absence of a Pm1174 gene homolog in the Pm strains P-934 and P-1059 (FIG. 2). This is another example of strain-based variation of glycosyltransferase genes which have been observed for many other bacteria.

Expression and Purification of Full Length PmST3 as PmST3-$His_6$ and MBP-PmST3-$His_6$ Fusion Proteins.

Initially, the full length Pm1174 gene was cloned into pET22b(+) using a synthetic gene with codons optimized for *E. coli* expression system as the template for PCR. The codon-optimized Pm1174 gene contains 30% adenine, 18% cytosine, 21% guanine and 31% thymine (FIG. 3) in comparison to the original sequence containing 35% adenine, 17% cytosine, 14% guanine and 34% thymine (GenBank accession no. AE004439). The full-length C-$His_6$-tagged PmST3 (PmST3-$His_6$) was expressed at 20° C. for 18 h with vigorous shaking (250 rpm) after induction with isopropyl-thio-β-D-galactopyranose (IPTG, 0.1 mM). Only a small amount (<1 mg) of soluble PmST3-$His_6$ was obtained by $Ni^{2+}$-NTA column purification from lysate obtained from one liter of *E. coli* cell culture grew in LB medium (10 g NaCl, 5 g yeast extract, and 10 g tryptone). Higher expression level of soluble protein was achieved by introducing an N-terminal maltose binding protein (MBP) to the full-length C-terminal His-tagged fusion protein by cloning using pMal-cX4 vector. Under the same expression conditions, 3 mg of MBP-PmST3-$His_6$ was routinely obtained by $Ni^{2+}$-NTA column purification using cell lysate from one liter of culture. The α2-3-sialyltransferase activity of both full length proteins were confirmed by thin-layer chromatography (TLC) and high-performance liquid chromatography (HPLC) studies as described previously (*Glycobiology,* 21:1206-1216; *J Am Chem Soc,* 127:17618-17619).

Protein Sequence Alignment of PmST3 with CstI, CstII, and Lic3B.

Protein sequence alignment of PmST3 with several sialyltransferases in CAZy GT42 family showed that PmST3 shares 52% sequence identity to Lic3B from *Haemophilus influenzae*, a lipopolysaccharide bifunctional α2-3/8-sialyltransferase; 44% identity to CstII, a multifunctional α2-3/8-sialyltransferase from *Campylobacter jejuni* with α2-8-sialidase and α2-8-trans-sialidase activities (Cheng J, Yu H, Lau K, Huang S, Chokhawala H A, Li Y, Tiwari V K, Chen X. 2008. Multifunctionality of *Campylobacter jejuni* sialyltransferase CstII: characterization of GD3/GT3 oligosaccharide synthase, GD3 oligosaccharide sialidase, and trans-sialidase activities. Glycobiology, 18:686-697); and 34% identity to CstI, a monofunctional α2-3-sialyltransferase from *Campylobacter jejuni* (Chiu C P, Lairson L L, Gilbert M, Wakarchuk W W, Withers S G, Strynadka N C. 2007. Structural analysis of the alpha-2,3-sialyltransferase Cst-I from *Campylobacter jejuni* in apo and substrate-analogue bound forms. *Biochemistry,* 46:7196-7204) (FIG. 4).

Improvement of the Expression Level of PmST3 by C-Terminal Truncations.

To further improve the expression of the soluble and active protein, three C-terminal truncated versions of PmST3 (PmST3Δ20-$His_6$, PmST3Δ35-$His_6$, and PmST3Δ45-$His_6$ with the removal of C-terminal 20, 35, and 45 amino acid residues) were cloned into pET22b(+) vector as C-$His_6$ (SEQ ID NO:37) tagged fusion proteins. PmST3Δ20-$His_6$ showed a slightly increased amount of purified protein but remained similar to that of the full-length protein. For PmST3Δ45-$His_6$, the expression of soluble protein was improved to the level of MBP fusion protein (4 mg of purified protein from 1 liter of cell culture by $Ni^{2+}$-NTA affinity chromatography). However, PmST3Δ45-$His_6$ seemed to have stability issues. Precipitation was observed after 3 days of storage at 4° C. after dialysis against a buffer (10% glycerol and 25 mM Tris-HCl, pH 7.5). PmST3Δ35-$His_6$ was found to be the optimal clone regarding protein expression and stability. Under the same expression conditions, purified PmST3Δ35-$His_6$ can be routinely obtained at a level of 29 mg from cell lysate from one liter of cell culture. The enzyme remained active after 3 months of storage in 10% glycerol and 25 mM Tris-HCl (pH 7.5) buffer. SDS-PAGE analysis indicated that the molecular weight of the purified protein (Error! Reference source not found.) is close to the calculated value of 33 kDa.

Example 2. PmST3 Activity Profiles

Materials and Methods pH profile of PmST3Δ35-$His_6$. Reactions were carried out in duplicate at 37° C. for 10 min. Each reaction mixture of a total volume of 10 μl contained a buffer (200 mM), an acceptor (1 mM, LacβPro2AA), a donor (1 mM, CMP-Neu5Ac), and PmST3Δ35-$His_6$ (0.45 μg $\mu l^{-1}$). Buffers used were: MES-KOH (pH 4.0-6.5), Tris-HCl (pH 7.0-9.0), and CHES (pH 10.0). Enzymatic reaction was quenched by adding 490 μl of pre-chilled acetonitrile:water (20:80) mixture. The samples were kept on ice until being analyzed by a Shimadzu LC-2010A HPLC system equipped with a membrane on-line degasser, a temperature control unit, and a fluorescence detector (the excitation wavelength was set at 315 nm and the emission wavelength was set at 400 nm) using a reverse phase Premier C18 column (250×4.6 mm I.D., 5 μm particle size, Shimadzu) protected with a C18 guard column cartridge. Mobile phase used was 20% acetonitrile in water.

Effects of Metal Ions, EDTA, and a Reducing Reagent DTT on the Activity of PmST3Δ35-$His_6$.

Reactions were carried out in duplicate at 37° C. for 10 min in a total volume of 10 μl in a Tris-HCl buffer (150 mM, pH 7.5) containing LacβPro2AA (1 mM), CMP-Neu5Ac (1 mM), and PmST3Δ35-$His_6$ (0.25 μg $\mu l^{-1}$). For metal effects, various concentrations (1, 5, 10, or 20 mM) of $MgCl_2$ or $MnCl_2$ were used. Ethylenediaminetetraacetic acid (EDTA) as a chelating agent was used at two concentrations (1 or 10 mM). A reducing reagent dithiothreitol (DTT) was used at two concentrations (1 or 10 mM). Reaction without metal ions, EDTA, or DTT was used as a control. The reaction was quenched by adding 490 μl of pre-chilled acetonitrile:water (20:80). Samples were kept on ice until being analyzed by HPLC equipped with a fluorescent detector (315 nm excitation and 400 nm emission).

Kinetic Studies of PmST3Δ35-$His_6$.

Reactions were carried out in duplicate at 37° C. for 7 min in a total volume of 10 μl in a Tris-HCl buffer (200 mM, pH 7.5). To obtain apparent kinetic parameters with CMP-Neu5Ac as the donor and LacβPro2AA as the acceptor, various concentrations (0.1, 0.2, 0.5, 1.0, 2.0, and 4.0 mM) of CMP-Neu5Ac with a fixed concentration (1 mM) of LacβPro2AA or various concentrations of LacβPro2AA (0.2, 0.4, 1.0, 2.0, 5.0, 10.0, and 20.0 mM) with a fixed concentration (1 mM) of CMP-Neu5Ac were used in the presence of 6.0 μM of PmST3Δ35-$His_6$. When Galβ1-3GlcNAcβPro2AA was used as the acceptor, apparent kinetic parameters were obtained by varying the concentrations of Galβ1-3GlcNAcβPro2AA (1.0, 10.0, 25.0, 50.0, and 100.0 mM) with a fixed concentration (1 mM) of CMP-Neu5Ac in the presence of 22.5 μM of PmST3Δ35-$His_6$.

Results

Effects of pH, Divalent Metal Ions, EDTA, and DTT on PmST3Δ5-$His_6$ Activity.

Figure 6:
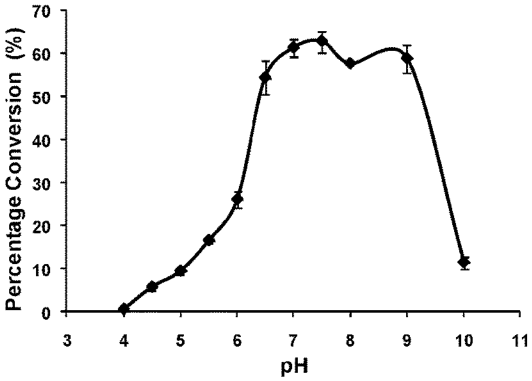
FIG. 6 shows the pH profile of PmST3Δ35-$His_6$. Buffers (200 mM) used: MES-KOH (pH 4.0-6.5), Tris-HCl (pH 7.0-9.0), and CHES (pH 10.0).

When LacβPro2AA was used as an acceptor, PmST3Δ35-$His_6$ was found to have an optimal pH range of 6.5-9.0 for its α2-3-sialyltransferase activity (FIG. 6). Activity decreased dramatically when pH was below 6.0 or reached 10.0. In comparison, PmST1 had a similar optimal pH range of 6.5-9.0 although at least 50% of the optimal activity remaining at pH 6.0 and 9.5-10.0. In comparison, PmST2 had a broader optimal pH range of 5.0-9.0 with at least 50% of the optimal activity remaining at pH 4.5.

Figure 7:
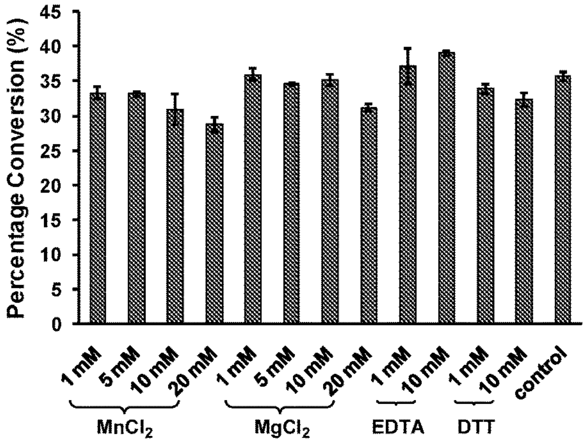
FIG. 7 shows the effects of divalent metals ($Mn^{2+}$ and $Mg^{2+}$), EDTA, and DTT on the activity of PmST3Δ35-$His_6$.

Similar to other reported sialyltransferases, PmST3Δ35-$His_6$ does not require a divalent metal ion for its activity as addition of a metal chelator EDTA for up to 10 mM did not affect the enzyme activity (FIG. 7). Like PmST2, the addition of $MnCl_2$ or $MgCl_2$ for up to 20 mM did not affect the activity of PmST3. On the contrary, the addition of $MnCl_2$ (5 mM or 10 mM) decreased the α2-3-sialyltransferase activity of PmST1 significantly and adding 20 mM of $MnCl_2$ almost abolished the α2-3-sialyltransferase activity completely. Change of activity was not observed with the addition of a reducing reagent DTT despite of the presence of three cysteine residues in the PmST3 protein sequence.

Apparent Kinetic Parameters for PmST3Δ35-$His_6$.

As shown in Table 2, PmST3Δ35-$His_6$ has the preference for β1-4-linked galactosides such as Galβ1-4GlcβPro2AA (LacβPro2AA) acceptor ($K_m$=4.9±0.6 mM) compared to β1-3-linked galactosides such as Galβ1-3GlcNAcβPro2AA acceptor ($K_m$=14±1 mM). With a 2.9-fold lower $K_m$ value and a 3-fold higher $k_{cat}$ value, β1-4-linked galactoside Galβ1-4GlcβPro2AA (LacβPro2AA, $k_{cat}/K_m$=9.2 $min^{-1}$ $mM^{-1}$) is a much better acceptor than β1-3-linked galactoside Galβ1-3GlcNAcβPro2AA ($k_{cat}/K_m$=1.0 $min^{-1}$ $mM^{-1}$). Among three *P. multocida* sialyltransferases, PmST3Δ35-$His_6$ has the highest binding affinity for CMP-Neu5Ac ($K_m$=0.26±0.01 mM) compared to PmST1 ($K_m$=0.44 mM) and PmST2 ($K_m$=1.3±0.1 mM). The binding affinity of PmST3Δ35-$His_6$ towards CMP-Neu5Ac is also higher than that of the truncated monofunctional α2-3-sialyltransferase CstI ($K_m$=0.4 mM) which shares 37% sequence identity to PmST3.

TABLE 2

Apparent kinetic parameters for PmST3Δ35-$His_6$.

| Substrates | CMP-Neu5Ac | LacβPro2AA | Galβ1-3GlcNAcβPro2AA |
|---|---|---|---|
| $V_{max}$ (mM $min^{-1}$) | (4.4 ± 0.1) × $10^{-2}$ | 0.27 ± 0.02 | 0.34 ± 0.02 |
| $K_m$ (mM) | 0.26 ± 0.01 | 4.9 ± 0.6 | 14 ± 1 |
| $k_{cat}$ ($min^{-1}$) | 7.3 ± 0.1 | 45 ± 3 | 15 ± 1 |
| $k_{cat}/K_m$ ($min^{-1}$ $mM^{-1}$) | 28 | 9.2 | 1.0 |

Example 3. Synthesis of Glycoconjugates

Materials and Methods

Substrate Specificities of PmST3Δ35-$His_6$.

All reactions were carried out in duplicate at 37° C. in Tris-HCl (200 mM, pH 7.5) containing an acceptor substrate (2 mM), CMP-Neu5Ac (2 mM), and PmST3Δ35-$His_6$ (0.25 μg $\mu l^{-1}$). At 10 min or 4 hr, aliquots of reaction mixture were withdrawn and added to pre-chilled acetonitrile:water (20:80) (for reactions with acceptors containing 2-aminobenzoic acid (2AA) or 4-methylumbelliferone (MU) aglycone) or pre-chilled 95% ethanol (for reactions with acceptor containing Pro-triazole-C14 or pNP aglycone) and samples were kept on ice until being analyzed. Samples with acceptors containing 2AA (315 nm excitation and 400 nm emission) or MU (326 nm excitation and 372 nm emission) were analyzed by HPLC equipped with a fluorescent detector. Samples with acceptor containing Pro-triazole-C14 (214 nm) or pNP (300 nm) aglycone were centrifuged at 13,000 rpm for 5 min and analyzed by capillary electrophoresis (CE) equipped with a photodiode array (PDA) detector as described previously using sodium borate buffer (50 mM, pH 10.2) containing β-cyclcodextrin (20 mM) as a running buffer (*Glycobiology,* 21:1206-1216).

Results

Acceptor Substrate Specificity of PmST3Δ35-$His_6$.

A list of monosaccharides and disaccharides containing different aglycons (a long hydrocarbon chain Pro-triazole-C14, Pro2AA, MU, and pNP) were used to investigate the substrate specificity of PmST3Δ35-$His_6$ (Table 3). Consistent with the kinetic data in Table 2, β1-4-linked galactosides including Galβ1-4GlcβOR (LacβOR) and Galβ1-4GlcNAcβOR (LacNAcβOR) are preferred acceptor substrates of the enzyme irrespective of the type of aglycones. Among all glycans tested, monosaccharide glycosides such as those with a galactose (Gal) or an N-acetyl galactosamine (GalNAc) were the least tolerated. Overall, the preference towards β1-4-linked galactoside acceptors is shared between PmST2 and PmST3. Unlike PmST1 which does not use lipid-containing acceptors efficiently or PmST2 which does not use oligosaccharide acceptor efficiently, galactosylated glycolipids and oligosaccharides are both suitable substrates for PmST3.

TABLE 3

Acceptor substrate specificity of PmST3Δ35-$His_6$.

| Substrates | % Conv. (10 min) | % Conv. (4 h) |
|---|---|---|
| LacβPro2AA | 30.4 ± 1.3 | 64.8 ± 0.4 |
| LacβMU | 29.9 ± 1.2 | 65.6 ± 1.6 |
| LacβPro-triazole-C14 | 21.5 ± 1.9 | 57.8 ± 0.5 |
| LacNAcβPro2AA | 34.4 ± 1.9 | 73.9 ± 1.6 |
| LacNAcβPro-triazole-C14 | 29.5 ± 2.4 | 76.9 ± 1.8 |
| Galβ1-3GlcNAcβPro2AA (LNBβPro2AA) | <6 | 23.3 ± 2.0 |
| Galβ1-3 GlcNAcβPro-triazole-C14 (LNBβC14) | <6 | 28.2 ± 1.5 |
| Galβ1-3 GlcNAcαPro-triazole-C14 (LNBαC14) | <1 | 8.7 ± 0.9 |
| Galβ1-3GalNAcαPro-triazole-C14 (GNBαC14) | <3 | 13.9 ± 0.2 |
| GalβPro-triazole-C14 | <1 | <6 |
| GalβpNP | <1 | 9.4 ± 0.4 |
| GalNAcαPro2AA | <1 | <5 |

As the key enzymes for the formation of α-linked sialic acid-containing structures in nature, sialyltransferases catalyze the formation of α2-3/6/8/9-sialyl linkages with high stereo- and regio-specificities. Despite of their different functions on catalyzing the formation of various sialyl linkages with distinctive acceptors, all eukaryotic sialyltransferases share some protein sequence homology and have all been grouped together with some viral sialyltransferases in a single glycosyltransferase family GT29 in the Carbohydrate-Active enZymes (CAZy) database. In comparison, bacterial sialyltransferases share little similarity to mammalian enzymes. They have more sequence diversity and are distributed into GT4, GT38, GT42, GT52, and GT80 five glycosyltransferase families. Except for several bacterial polysialyltransferases which have been grouped into GT4 and GT38 families, all bacterial sialyltransferases characterized to date belong to GT42, GT52, and GT80 three GT families.

Three sialyltransferases characterized from *Pasteurella multocida* do not share sequence homology and are grouped into three different CAZy GT families. As shown in Table 4, different from PmST1 which belongs to GT80 family and PmST2 which belongs to GT52 family, the Pm1174 gene of *P. multocida* str. 70 (Pm70) has been determined to encode a monofunctional α2-3-sialyltransferase belonging to GT42 family. Functional wise, PmST3 is also different from PmST1 and PmST2. For example, PmST1 is a multifunctional enzyme which has a major α2-3-sialyltransferase activity in addition to its α2-6-sialyltransferase, α2-3-sialidase, and α2-3-trans-sialidase activities. In comparison, both PmST2 and PmST3 are monofunctional α2-3-sialyltransferases. Quite interestingly, these three PmSTs also have different substrate preferences. PmST1 seems to use a broad array of non-lipid-containing galactosides including monosaccharide galactosides, but not glycolipids, as suitable acceptors. In contrast, PmST2 prefers glycolipids containing a terminal β1-4-linked galactose as acceptors while galactosyl oligosaccharides and Galβ1-3-linked glycolipids are poor acceptors. PmST3 is sort of a "hybrid" of PmST1 and PmST2 in respect of its substrate specificity. It can use both galactosyl oligosaccharides and glycolipids as acceptors effectively. Despite the discovery and characterization of three functional sialyltransferases from Pm, sialic acid has not been found in the CPS or LOS structures characterized to date. It will be interesting to identify the native acceptors for Pm sialyltransferases and investigate the importance of sialyltransferases in Pm infection process and survival.

TABLE 4

Comparison of three *Pasteurella multocida* sialyltransferases.

| Enzymes | Δ25PmST1-$His_6$ | MBP-PmST2-$His_6$ | PmST3Δ35-$His_6$ |
|---|---|---|---|
| Gene is found in strain Pm70[a] | Yes (Pm0188) | Yes (Pm0508) | Yes (Pm1174) |
| Gene is found in strain P-1059 | Yes | Yes | No |
| CAZy GT family | GT80 | GT52 | GT42 |
| Expression level (mg/L culture) | 100 | 21 | 29 |
| α2-3-sialyltransferase activity | Yes | Yes | Yes |
| α2-6-sialyltransferase activity | Yes | No | No |
| α2-3-sialidase activity | Yes | No | No |
| α2-3-trans-sialidase activity | Yes | No | No |
| Use galactosyl oligosaccharides as acceptors | Yes | Very weak activity | Yes |
| Use galactosyl glycolipids as acceptors | Very weak activity | Yes | Yes |

[a]Gene names are listed in parentheses.

The numbers of sialyltransferases seem to vary among different Pm strains. While PmST1 and PmST2 encoded by homologs of Pm strain Pm70 genes Pm0188 and Pm0508, respectively, have been cloned from Pm strain P-1059, a homolog of Pm1174 gene from Pm strain Pm70 (a serogroup A strain) encoding PmST3 seems to be missing from genomic DNA sequence of Pm strains P-1059 (an A:3 strain) and P-934 (a serogroup D strain).

Among sialyltransferases in CAZy GT42 family, PmST3 shares the highest amino acid identity (52%) to Lic3B from *Haemophilus influenzae*, a lipopolysaccharide bifunctional α2-3/8-sialyltransferase. It also has a relatively high amino acid identity (44%) compared to CstII, a multifunctional α2-3/8-sialyltransferase from *Campylobacter jejuni* with α2-8-sialidase and α2-8-trans-sialidase activities. Although both are monofunctional α2-3-sialyltransferases, PmST3 and CstI only shares 34% amino acid identity (FIG. 4).

In addition to the crystal structure of a porcine ST3Gal-I, a GT29 family mammalian sialyltransferase, structures of several bacterial sialyltransferases from GT42, GT80, and more recently GT52 glycosyltransferase families have been reported. Unlike sialyltransferases from GT80 (e.g. PmST1, α2-6-sialyltransferase from *Photobacterium* sp. JT-ISH-224, and α2-3-sialyltransferase from *Photobacterium phosphoreum*) and GT52 (e.g. α2-3/6-sialyltransferase from *Neisseria meningitidis*) families which adopt a GT-B fold consisting of two Rossmann-like domains, sialyltransferases from GT42 family (e.g. CstII and CstI) and GT29 family (e.g. porcine ST3Gal-I) adopt variants of a GT-A fold consisting of a single Rossmann-like fold. While an aspartate residue is indicated to be the catalytic base in PmST1 (Asp141), *Photobacterium* sp. JT-ISH-224 α2,6-sialyltransferase (Asp232), and *N. meningitidis* α2-3/6-sialyltransferase (Asp258) with a GT-B fold, a histidine residue is the catalytic base in CstII (His188) and the porcine ST3Gal-I (His319 in the VS sialyl motif) with GT-A variant folds.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

SEQUENCE LISTING (PmST3)

SEQ ID NO: 1

```
ATGGATAAATTTGCCGAACATGAAATTCCGAAAGCCGTTATTGTTGCAGG
TAATGGTGAAAGCCTGAGCCAGATTGATTATCGTCTGCTGCCGAAAAATT
ATGATGTGTTTCGCTGCAATCAGTTTTATTTTGAAGAACGCTATTTTCTG
GGCAATAAAATTAAAGCCGTGTTTTTTACACCGGGTGTTTTTCTGGAACA
GTATTATACCCTGTATCATCTGAAACGCAATAATGAATATTTTGTGGATA
ATGTGATTCTGAGCAGCTTTAATCATCCGACCGTTGATCTGGAAAAAAGC
CAGAAAATTCAGGCCCTGTTTATTGATGTGATTAATGGCTATGAAAAATA
TCTGAGCAAACTGACCGCCTTTGATGTTTATCTGCGCTATAAAGAACTGT
ATGAAAATCAGCGTATTACCAGCGGTGTTTATATGTGTGCAGTTGCAATT
GCAATGGGCTATACCGATATTTATCTGACCGGCATTGATTTTTATCAGGC
CAGCGAAGAAAATTATGCCTTTGATAATAAAAAACCGAATATTATTCGCC
TGCTGCCGGATTTTCGCAAAGAAAAAACCCTGTTTAGCTATCATAGCAAA
GATATTGATCTGGAAGCCCTGAGCTTTCTGCAGCAGCATTATCATGTGAA
TTTTTATAGCATTAGCCCGATGAGTCCGCTGAGCAAACATTTTCCGATTC
CGACCGTGGAAGATGATTGTGAAACCACCTTTGTTGCACCGCTGAAAGAA
AATTATATTAATGATATTCTGCTGCCTCCGCATTTTGTGTATGAAAAACT
GGGCACCATTGTGAGCAAAAAAAGCCGTTTTCATAGCAATCTGATTGTGC
GTCTGATTCGTGATCTGCTGAAACTGCCGAGCGCACTGAAACATTATCTG
AAAGAAAAATAA
```

(PmST3-$His_6$)

SEQ ID NO: 2

```
ATGGATAAATTTGCCGAACATGAAATTCCGAAAGCCGTTATTGTTGCAGG
TAATGGTGAAAGCCTGAGCCAGATTGATTATCGTCTGCTGCCGAAAAATT
ATGATGTGTTTCGCTGCAATCAGTTTTATTTTGAAGAACGCTATTTTCTG
GGCAATAAAATTAAAGCCGTGTTTTTTACACCGGGTGTTTTTCTGGAACA
GTATTATACCCTGTATCATCTGAAACGCAATAATGAATATTTTGTGGATA
ATGTGATTCTGAGCAGCTTTAATCATCCGACCGTTGATCTGGAAAAAAGC
CAGAAAATTCAGGCCCTGTTTATTGATGTGATTAATGGCTATGAAAAATA
TCTGAGCAAACTGACCGCCTTTGATGTTTATCTGCGCTATAAAGAACTGT
ATGAAAATCAGCGTATTACCAGCGGTGTTTATATGTGTGCAGTTGCAATT
GCAATGGGCTATACCGATATTTATCTGACCGGCATTGATTTTTATCAGGC
CAGCGAAGAAAATTATGCCTTTGATAATAAAAAACCGAATATTATTCGCC
TGCTGCCGGATTTTCGCAAAGAAAAAACCCTGTTTAGCTATCATAGCAAA
GATATTGATCTGGAAGCCCTGAGCTTTCTGCAGCAGCATTATCATGTGAA
TTTTTATAGCATTAGCCCGATGAGTCCGCTGAGCAAACATTTTCCGATTC
CGACCGTGGAAGATGATTGTGAAACCACCTTTGTTGCACCGCTGAAAGAA
AATTATATTAATGATATTCTGCTGCCTCCGCATTTTGTGTATGAAAAACT
GGGCACCATTGTGAGCAAAAAAAGCCGTTTTCATAGCAATCTGATTGTGC
GTCTGATTCGTGATCTGCTGAAACTGCCGAGCGCACTGAAACATTATCTG
AAAGAAAAACTCGAGCACCACCACCACCACCACTGA
```

(MBP-PmST3-$His_6$)

SEQ ID NO: 3

```
atgaaaatcgaagaaggtaaactggtaatctggattaacggcgataaagg
ctataacggtctcgctgaagteggtaagaaattcgagaaagataccggaa
ttaaagtcaccgttgagcatccggataaactggaagagaaattcccacag
gttgeggcaactggcgatggccctgacattatcttctgggcacacgaccg
ctttggtggctacgctcaatctggcctgttggctgaaatcaccccggaca
aagcgttccaggacaagctgtatccgtttacctgggatgccgtacgttac
aacggcaagctgattgcttacccgatcgctgttgaagcgttatcgctgat
ttataacaaagatctgctgccgaacccgccaaaaacctgggaagagatcc
cggcgctggataaagaactgaaagcgaaaggtaagagcgcgctgatgttc
aacctgcaagaaccgtacttcacctggccgctgattgctgctgacggggg
ttatgcgttcaagtatgaaaacggcaagtacgacattaaagacgtgggcg
```

-continued

```
tggataacgctggcgcgaaagcgggtctgaccttcctggttgacctgatt
aaaaacaaacacatgaatgcagacaccgattactccatcgcagaagctgc
ctttaataaaggcgaaacagcgatgaccatcaacggcccgtgggcatggt
ccaacatcgacaccagcaaagtgaattatggtgtaacggtactgccgacc
ttcaagggtcaaccatccaaaccgttcgttggcgtgctgagcgcaggtat
taacgccgccagtccgaacaaagagctggcaaaagagttcctcgaaaact
atctgctgactgatgaaggtctggaagcggttaataaagacaaaccgctg
ggtgccgtagcgctgaagtcttacgaggaagagttggtgaaagatccgcg
gattgccgccactatggaaaacgcccagaaaggtgaaatcatgccgaaca
tcccgcagatgtccgctttctggtatgccgtgcgtactgcggtgatcaacg
ccgccagcggtcgtcagactgtcgatgaagccctgaaagacgcgcagact
aattcgagctcgaacaacaacaacaataacaataacaacaacctcgggat
cgagggaaggatttcagaattcATGGATAAATTTGCCGAACATGAAATTC
CGAAAGCCGTTATTGTTGCAGGTAATGGTGAAAGCCTGAGCCAGATTGAT
TATCGTCTGCTGCCGAAAAATTATGATGTGTTTCGCTGCAATCAGTTTTA
TTTTGAAGAACGCTATTTTCTGGGCAATAAAATTAAAGCCGTGTTTTTTA
CACCGGGTGTTTTTCTGGAACAGTATTATACCCTGTATCATCTGAAACGC
AATAATGAATATTTTGTGGATAATGTGATTCTGAGCAGCTTTAATCATCC
GACCGTTGATCTGGAAAAAAGCCAGAAAATTCAGGCCCTGTTTATTGATG
TGATTAATGGCTATGAAAAATATCTGAGCAAACTGACCGCCTTTGATGTT
TATCTGCGCTATAAAGAACTGTATGAAAATCAGCGTATTACCAGCGGTGT
TTATATGTGTGCAGTTGCAATTGCAATGGGCTATACCGATATTTATCTGA
CCGGCATTGATTTTTATCAGGCCAGCGAAGAAAATTATGCCTTTGATAAT
AAAAAACCGAATATTATTCGCCTGCTGCCGGATTTTCGCAAAGAAAAAAC
CCTGTTTAGCTATCATAGCAAAGATATTGATCTGGAAGCCCTGAGCTTTC
TGCAGCAGCATTATCATGTGAATTTTTATAGCATTAGCCCGATGAGTCCG
CTGAGCAAACATTTTCCGATTCCGACCGTGGAAGATGATTGTGAAACCAC
CTTTGTTGCACCGCTGAAAGAAAATTATATTAATGATATTCTGCTGCCTC
CGCATTTTGTGTATGAAAAACTGGGCACCATTGTGAGCAAAAAAAGCCGT
TTCATAGCAATCTGATTGTGCGTCTGATTCGTGATCTGCTGAAACTGCC
GAGCGCACTGAAACATTATCTGAAAGAAAAACACCACCACCACCACCACC
ACCACCACTAA
```

(PmST3Δ20-His$_6$)

SEQ ID NO: 4

```
ATGGATAAATTTGCCGAACATGAAATTCCGAAAGCCGTTATTGTTGCAGG
TAATGGTGAAAGCCTGAGCCAGATTGATTATCGTCTGCTGCCGAAAAATT
ATGATGTGTTTCGCTGCAATCAGTTTTATTTTGAAGAACGCTATTTTCTG
GGCAATAAAATTAAAGCCGTGTTTTTTACACCGGGTGTTTTTCTGGAACA
GTATTATACCCTGTATCATCTGAAACGCAATAATGAATATTTTGTGGATA
ATGTGATTCTGAGCAGCTTTAATCATCCGACCGTTGATCTGGAAAAAAGC
CAGAAAATTCAGGCCCTGTTTATTGATGTGATTAATGGCTATGAAAAATA
TCTGAGCAAACTGACCGCCTTTGATGTTTATCTGCGCTATAAAGAACTGT
ATGAAAATCAGCGTATTACCAGCGGTGTTTATATGTGTGCAGTTGCAATT
GCAATGGGCTATACCGATATTTATCTGACCGGCATTGATTTTTATCAGGC
CAGCGAAGAAAATTATGCCTTTGATAATAAAAAACCGAATATTATTCGCC
TGCTGCCGGATTTTCGCAAAGAAAAAACCCTGTTTAGCTATCATAGCAAA
GATATTGATCTGGAAGCCCTGAGCTTTCTGCAGCAGCATTATCATGTGAA
TTTTTATAGCATTAGCCCGATGAGTCCGCTGAGCAAACATTTTCCGATTC
CGACCGTGGAAGATGATTGTGAAACCACCTTTGTTGCACCGCTGAAAGAA
AATTATATTAATGATATTCTGCTGCCTCCGCATTTTGTGTATGAAAAACT
GGGCACCATTGTGAGCAAAAAAAGCCGTTTTCATAGCAATCTGATTGTGG
TCGACAAGCTTGCGGCCGCACTCGAGCACCACCACCACCACCACTGA
```

(PmST3Δ35-His$_6$)

SEQ ID NO: 5

```
ATGGATAAATTTGCCGAACATGAAATTCCGAAAGCCGTTATTGTTGCAGG
TAATGGTGAAAGCCTGAGCCAGATTGATTATCGTCTGCTGCCGAAAAATT
ATGATGTGTTTCGCTGCAATCAGTTTTATTTTGAAGAACGCTATTTTCTG
GGCAATAAAATTAAAGCCGTGTTTTTTACACCGGGTGTTTTTCTGGAACA
GTATTATACCCTGTATCATCTGAAACGCAATAATGAATATTTTGTGGATA
ATGTGATTCTGAGCAGCTTTAATCATCCGACCGTTGATCTGGAAAAAAGC
CAGAAAATTCAGGCCCTGTTTATTGATGTGATTAATGGCTATGAAAAATA
TCTGAGCAAACTGACCGCCTTTGATGTTTATCTGCGCTATAAAGAACTGT
ATGAAAATCAGCGTATTACCAGCGGTGTTTATATGTGTGCAGTTGCAATT
GCAATGGGCTATACCGATATTTATCTGACCGGCATTGATTTTTATCAGGC
CAGCGAAGAAAATTATGCCTTTGATAATAAAAAACCGAATATTATTCGCC
TGCTGCCGGATTTTCGCAAAGAAAAAACCCTGTTTAGCTATCATAGCAAA
GATATTGATCTGGAAGCCCTGAGCTTTCTGCAGCAGCATTATCATGTGAA
TTTTTATAGCATTAGCCCGATGAGTCCGCTGAGCAAACATTTTCCGATTC
CGACCGTGGAAGATGATTGTGAAACCACCTTTGTTGCACCGCTGAAAGAA
AATTATATTAATGATATTCTGCTGCCTCCGCATTTTGTGTATGAAAAACT
GGGCGTCGACAAGCTTGCGGCCGCACTCGAGCACCACCACCACCACCACT
GA
```

-continued (PmST3Δ45-His$_6$)

SEQ ID NO: 6

```
ATGGATAAATTTGCCGAACATGAAATTCCGAAAGCCGTTATTGTTGCAGG
TAATGGTGAAAGCCTGAGCCAGATTGATTATCGTCTGCTGCCGAAAAATT
ATGATGTGTTTCGCTGCAATCAGTTTTATTTTGAAGAACGCTATTTTCTG
GGCAATAAAATTAAAGCCGTGTTTTTTACACCGGGTGTTTTTCTGGAACA
GTATTATACCCTGTATCATCTGAAACGCAATAATGAATATTTTGTGGATA
ATGTGATTCTGAGCAGCTTTAATCATCCGACCGTTGATCTGGAAAAAAGC
CAGAAAATTCAGGCCCTGTTTATTGATGTGATTAATGGCTATGAAAAATA
TCTGAGCAAACTGACCGCCTTTGATGTTTATCTGCGCTATAAAGAACTGT
ATGAAAATCAGCGTATTACCAGCGGTGTTTATATGTGTGCAGTTGCAATT
GCAATGGGCTATACCGATATTTATCTGACCGGCATTGATTTTTATCAGGC
CAGCGAAGAAAATTATGCCTTTGATAATAAAAAACCGAATATTATTCGCC
TGCTGCCGGATTTTCGCAAAGAAAAAACCCTGTTTAGCTATCATAGCAAA
GATATTGATCTGGAAGCCCTGAGCTTTCTGCAGCAGCATTATCATGTGAA
TTTTTATAGCATTAGCCCGATGAGTCCGCTGAGCAAACATTTTCCGATTC
CGACCGTGGAAGATGATTGTGAAACCACCTTTGTTGCACCGCTGAAAGAA
AATTATATTAATGATATTCTGCTGGTCGACAAGCTTGCGGCCGCACTCGA
GCACCACCACCACCACCACTGA
```

(PmST3)

SEQ ID NO: 7

```
MDKFAEHEIPKAVIVAGNGESLSQIDYRLLPKNYDVFRCNQFYFEERYFL
GNKIKAVFFTPGVFLEQYYTLYHLKRNNEYFVDNVILSSFNHPTVDLEKS
QKIQALFIDVINGYEKYLSKLTAFDVYLRYKELYENQRITSGVYMCAVAI
AMGYTDIYLTGIDFYQASEENYAFDNKKPNIIRLLPDFRKEKTLFSYHSK
DIDLEALSFLQQHYHVNFYSISPMSPLSKHFPIPTVEDDCETTFVAPLKE
NYINDILLPPHFVYEKLGTIVSKKSRFHSNLIVRLIRDLLKLPSALKHYL
KEK
```

(PmST3-His$_6$)

SEQ ID NO: 8

```
MDKFAEHEIPKAVIVAGNGESLSQIDYRLLPKNYDVFRCNQFYFEERYFL
GNKIKAVFFTPGVFLEQYYTLYHLKRNNEYFVDNVILSSFNHPTVDLEKS
QKIQALFIDVINGYEKYLSKLTAFDVYLRYKELYENQRITSGVYMCAVAI
AMGYTDIYLTGIDFYQASEENYAFDNKKPNIIRLLPDFRKEKTLFSYHSK
DIDLEALSFLQQHYHVNFYSISPMSPLSKHFPIPTVEDDCETTFVAPLKE
NYINDILLPPHFVYEKLGTIVSKKSRFHSNLIVRLIRDLLKLPSALKHYL
KEKLEHHHHHH
```

(MBP-PmST3-His$_6$)

SEQ ID NO: 9

```
MKIEEGKLVIWINGDKGYNGLAEVGKKFEKDTGIKVTVEHPDKLEEKFPQ
VAATGDGPDIIFWAHDRFGGYAQSGLLAEITPDKAFQDKLYPFTWDAVRY
NGKLIAYPIAVEALSLIYNKDLLPNPPKTWEEIPALDKELKAKGKSALMF
NLQEPYFTWPLIAADGGYAFKYENGKYDIKDVGVDNAGAKAGLTFLVDLI
KNKHMNADTDYSIAEAAFNKGETAMTINGPWAWSNIDTSKVNYGVTVLPT
FKGQPSKPFVGVLSAGINAASPNKELAKEFLENYLLTDEGLEAVNKDKPL
GAVALKSYEEELVKDPRIAATMENAQKGEIMPNIPQMSAFWYAVRTAVIN
AASGRQTVDEALKDAQTNSSSNNLGIEGRISEFMDKFAEHEIPKAVIVAG
NGESLSQIDYRLLPKNYDVFRCNQFYFEERYFLGNKIKAVFFTPGVFLEQ
YYTLYHLKRNNEYFVDNVILSSFNHPTVDLEKSQKIQALFIDVINGYEKY
LSKLTAFDVYLRYKELYENQRITSGVYMCAVAIAMGYTDIYLTGIDFYQA
SEENYAFDNKKPNIIRLLPDFRKEKTLFSYHSKDIDLEALSFLQQHYHVN
FYSISPMSPLSKHFPIPTVEDDCETTFVAPLKENYINDILLPPHFVYEKL
GTIVSKKSRFHSNLIVRLIRDLLKLPSALKHYLKEKHHHHHH
```

(PmST3Δ20-His$_6$)

SEQ ID NO: 10

```
MDKFAEHEIPKAVIVAGNGESLSQIDYRLLPKNYDVFRCNQFYFEERYF
LGNKIKAVFFTPGVFLEQYYTLYHLKRNNEYFVDNVILSSFNHPTVDLE
KSQKIQALFIDVINGYEKYLSKLTAFDVYLRYKELYENQRITSGVYMCA
VAIAMGYTDIYLTGIDFYQASEENYAFDNKKPNIIRLLPDFRKEKTLFS
YHSKDIDLEALSFLQQHYHVNFYSISPMSPLSKHFPIPTVEDDCETTFV
APLKENYINDILLPPHFVYEKLGTIVSKKSRFHSNLIVVDKLAAALEHH
HHHH
```

(PmST3Δ35-His$_6$)

SEQ ID NO: 11

```
MDKFAEHEIPKAVIVAGNGESLSQIDYRLLPKNYDVFRCNQFYFEERYF
LGNKIKAVFFTPGVFLEQYYTLYHLKRNNEYFVDNVILSSFNHPTVDLE
KSQKIQALFIDVINGYEKYLSKLTAFDVYLRYKELYENQRITSGVYMCA
VAIAMGYTDIYLTGIDFYQASEENYAFDNKKPNIIRLLPDFRKEKTLFS
YHSKDIDLEALSFLQQHYHVNFYSISPMSPLSKHFPIPTVEDDCETTFV
APLKENYINDILLPPHFVYEKLGVDKLAAALEHHHHHH
```

-continued (PmST3Δ45-His$_6$)

SEQ ID NO: 12

MDKFAEHEIPKAVIVAGNGESLSQIDYRLLPKNYDVFRCNQFYFEERYF
LGNKIKAVFFTPGVFLEQYYTLYHLKRNNEYFVDNVILSSFNHPTVDLE
KSQKIQALFIDVINGYEKYLSKLTAFDVYLRYKELYENQRITSGVYMCA
VAIAMGYTDIYLTGIDFYQASEENYAFDNKKPNIIRLLPDFRKEKTLFS
YHSKDIDLEALSFLQQHYHVNFYSISPMSPLSKHFPIPTVEDDCETTFV
APLKENYINDILLVDKLAAALEHHHHHH (sialyltransferase motif A)

SEQ ID NO: 13

GIDFYQ (sialyltransferase motif B)

SEQ ID NO: 14

YXF (X = A or P)

(sialyltransferse motif C)

SEQ ID NO: 15

HS (WTPmST3)

SEQ ID NO:16

ATGGATAAGTTCGCAGAACATGAAATACCGAAAGCCGTTATTGTTGCAGG
GAATGGCGAGAGTTTAAGTCAAATTGATTATAGGTTGTTACCGAAAAATT
ATGATGTGTTTCGTTGTAATCAATTTTATTTTGAAGAACGCTATTTTTTA
GGAAACAAGATAAAAGCAGTTTTCTTCACGCCAGGGGTCTTTCTTGAGCA
ATATTATACACTTTATCATCTCAAGAGAAACAATGAGTATTTTGTTGATA
ATGTGATTCTCTCTTCTTTTAATCATCCTACAGTAGATTTAGAAAAGAGT
CAGAAAATACAAGCACTTTTTATTGATGTGATCAACGGATATGAAAAGTA
TTTATCTAAACTCACTGCTTTTGATGTTTATTTGCGCTATAAAGAATTAT
ATGAGAATCAAAGAATTACATCTGGCGTATATATGTGTGCAGTTGCTATT
GCGATGGGATATACAGATATTTACTTAACTGGTATCGATTTTTATCAAGC
GAGCGAAGAAAACTACGCATTCGATAATAAAAAGCCTAACATTATTAGGT
TATTGCCTGATTTTCGGAAAGAAAAAACACTCTTTTCTTATCATAGTAAA
GATATTGATTTGGAAGCATTATCTTTTTTACAACAGCATTATCATGTTAA
TTTTTATTCAATTTCACCAATGAGCCCTTTGTCTAAACATTTTCCTATTC
CAACTGTAGAGGATGATTGTGAAACAACTTTTGTTGCGCCACTAAAAGAA
AATTACATTAATGATATATTGTTGCCTCCTCATTTTGTATATGAAAAATT
AGGGACCATCGTGTCTAAGAAATCACGTTTTCATTCTAACTTGATTGTCA
GGTTGATTAGAGACTTATTGAAATTACCGAGTGCACTTAAACACTATTTA
AAAGAAAAATAG (WTPmST3-His$_6$)

SEQ ID NO: 17

ATGGATAAGTTCGCAGAACATGAAATACCGAAAGCCGTTATTGTTGCAGG
GAATGGCGAGAGTTTAAGTCAAATTGATTATAGGTTGTTACCGAAAAATT
ATGATGTGTTTCGTTGTAATCAATTTTATTTTGAAGAACGCTATTTTTTA
GGAAACAAGATAAAAGCAGTTTTCTTCACGCCAGGGGTCTTTCTTGAGCA
ATATTATACACTTTATCATCTCAAGAGAAACAATGAGTATTTTGTTGATA
ATGTGATTCTCTCTTCTTTTAATCATCCTACAGTAGATTTAGAAAAGAGT
CAGAAAATACAAGCACTTTTTATTGATGTGATCAACGGATATGAAAAGTA
TTTATCTAAACTCACTGCTTTTGATGTTTATTTGCGCTATAAAGAATTAT
ATGAGAATCAAAGAATTACATCTGGCGTATATATGTGTGCAGTTGCTATT
GCGATGGGATATACAGATATTTACTTAACTGGTATCGATTTTTATCAAGC
GAGCGAAGAAAACTACGCATTCGATAATAAAAAGCCTAACATTATTAGGT
TATTGCCTGATTTTCGGAAAGAAAAAACACTCTTTTCTTATCATAGTAAA
GATATTGATTTGGAAGCATTATCTTTTTTACAACAGCATTATCATGTTAA
TTTTTATTCAATTTCACCAATGAGCCCTTTGTCTAAACATTTTCCTATTC
CAACTGTAGAGGATGATTGTGAAACAACTTTTGTTGCGCCACTAAAAGAA
AATTACATTAATGATATATTGTTGCCTCCTCATTTTGTATATGAAAAATT
AGGGACCATCGTGTCTAAGAAATCACGTTTTCATTCTAACTTGATTGTCA
GGTTGATTAGAGACTTATTGAAATTACCGAGTGCACTTAAACACTATTTA
AAAGAAAAACTCGAGCACCACCACCACCACCACTGA (MBP-WTPmST3-His$_6$)

SEQ ID NO: 18 atgaaaatcgaagaaggtaaactggtaatctggattaacggcgataaagg
ctataacggtctcgctgaagtcggtaagaaattcgagaaagataccggaa
ttaaagtcaccgttgagcatccggataaactggaagagaaattcccacag
gttgcggcaactggcgatggccctgacattatcttctgggcacacgaccg
ctttggtggctacgctcaatctggcctgttggctgaaatcaccccggaca
aagcgttccaggacaagctgtatccgtttacctgggatgccgtacgttac
aacggcaagctgattgcttacccgategctgttgaagcgttatcgctgat
ttataacaaagatctgctgccgaacccgccaaaaacctgggaagagatcc
cggcgctggataaagaactgaaagcgaaaggtaagagcgcgctgatgttc
aacctgcaagaaccgtacttcacctggccgctgattgctgctgacggggg
ttatgcgttcaagtatgaaaacggcaagtacgacattaaagacgtgggcg
tggataacgctggcgcgaaagcgggtctgaccttcctggttgacctgatt
aaaaacaaacacatgaatgcagacaccgattactccatcgcagaagctgc
ctttaataaaggcgaaacagcgatgaccatcaacggcccgtgggcatggt
ccaacatcgacaccagcaaagtgaattatggtgtaacggtactgccgacc
ttcaagggtcaaccatccaaaccgttcgttggcgtgctgagcgcaggtat
taacgccgccagtccgaacaaagagctggcaaaagagttectcgaaaact
atctgctgactgatgaaggtctggaageggttaataaagacaaaccgctg
ggtgccgtagcgctgaagtcttacgaggaagagttggtgaaagatccgcg
gattgccgccactatggaaaacgcccagaaaggtgaaatcatgccgaaca
tcccgcagatgtccgctttctggtatgccgtgcgtactgggtgatcaacg
ccgccagcggtcgtcagactgtcgatgaagccctgaaagacgcgcagact
aattcgagctcgaacaacaacaacaataacaataacaacaacctcgggat
cgagggaaggatttcagaattcATGGATAAGTTCGCAGAACATGAAATAC
CGAAAGCCGTTATTGTTGCAGGGAATGGCGAGAGTTTAAGTCAAATTGAT
TATAGGTTGTTACCGAAAAATTATGATGTGTTTCGTTGTAATCAATTTTA
TTTTGAAGAACGCTATTTTTTAGGAAACAAGATAAAAGCAGTTTTCTTCA
CGCCAGGGGTCTTTCTTGAGCAATATTATACACTTTATCATCTCAAGAGA
AACAATGAGTATTTTGTTGATAATGTGATTCTCTCTTCTTTTAATCATCC
TACAGTAGATTTAGAAAAGAGTCAGAAAATACAAGCACTTTTTATTGATG
TGATCAACGGATATGAAAAGTATTTATCTAAACTCACTGCTTTTGATGTT
TATTTGCGCTATAAAGAATTATATGAGAATCAAAGAATTACATCTGGCGT
ATATATGTGTGCAGTTGCTATTGCGATGGGATATACAGATATTTACTTAA
CTGGTATCGATTTTTATCAAGCGAGCGAAGAAAACTACGCATTCGATAAT
AAAAAGCCTAACATTATTAGGTTATTGCCTGATTTTCGGAAAGAAAAAAC
ACTCTTTTCTTATCATAGTAAAGATATTGATTTGGAAGCATTATCTTTTT
TACAACAGCATTATCATGTTAATTTTTATTCAATTTCACCAATGAGCCCT
TTGTCTAAACATTTTCCTATTCCAACTGTAGAGGATGATTGTGAAACAAC
TTTTGTTGCGCCACTAAAAGAAAATTACATTAATGATATATTGTTGCCTC
CTCATTTTGTATATGAAAAATTAGGGACCATCGTGTCTAAGAAATCACGT
TTTCATTCTAACTTGATTGTCAGGTTGATTAGAGACTTATTGAAATTACC
GAGTGCACTTAAACACTATTTAAAAGAAAAACACCACCACCACCACCACT
AA (WTPmST3Δ20-His$_6$)

SEQ ID NO: 19

ATGGATAAGTTCGCAGAACATGAAATACCGAAAGCCGTTATTGTTGCAGG
GAATGGCGAGAGTTTAAGTCAAATTGATTATAGGTTGTTACCGAAAAATT
ATGATGTGTTTCGTTGTAATCAATTTTATTTTGAAGAACGCTATTTTTTA
GGAAACAAGATAAAAGCAGTTTTCTTCACGCCAGGGGTCTTTCTTGAGCA
ATATTATACACTTTATCATCTCAAGAGAAACAATGAGTATTTTGTTGATA
ATGTGATTCTCTCTTCTTTTAATCATCCTACAGTAGATTTAGAAAAGAGT
CAGAAAATACAAGCACTTTTTATTGATGTGATCAACGGATATGAAAAGTA
TTTATCTAAACTCACTGCTTTTGATGTTTATTTGCGCTATAAAGAATTAT
ATGAGAATCAAAGAATTACATCTGGCGTATATATGTGTGCAGTTGCTATT
GCGATGGGATATACAGATATTTACTTAACTGGTATCGATTTTTATCAAGC
GAGCGAAGAAAACTACGCATTCGATAATAAAAAGCCTAACATTATTAGGT
TATTGCCTGATTTTCGGAAAGAAAAAACACTCTTTTCTTATCATAGTAAA
GATATTGATTTGGAAGCATTATCTTTTTTACAACAGCATTATCATGTTAA
TTTTTATTCAATTTCACCAATGAGCCCTTTGTCTAAACATTTTCCTATTC
CAACTGTAGAGGATGATTGTGAAACAACTTTTGTTGCGCCACTAAAAGAA
AATTACATTAATGATATATTGTTGCCTCCTCATTTTGTATATGAAAAATT
AGGGACCATCGTGTCTAAGAAATCACGTTTTCATTCTAACTTGATTGTCG
TCGACAAGCTTGCGGCCGCACTCGAGCACCACCACCACCACCACTGA (WTPmST3Δ35-His$_6$)

SEQ ID NO: 20

ATGGATAAGTTCGCAGAACATGAAATACCGAAAGCCGTTATTGTTGCAGG
GAATGGCGAGAGTTTAAGTCAAATTGATTATAGGTTGTTACCGAAAAATT
ATGATGTGTTTCGTTGTAATCAATTTTATTTTGAAGAACGCTATTTTTTA
GGAAACAAGATAAAAGCAGTTTTCTTCACGCCAGGGGTCTTTCTTGAGCA
ATATTATACACTTTATCATCTCAAGAGAAACAATGAGTATTTTGTTGATA
ATGTGATTCTCTCTTCTTTTAATCATCCTACAGTAGATTTAGAAAAGAGT
CAGAAAATACAAGCACTTTTTATTGATGTGATCAACGGATATGAAAAGTA
TTTATCTAAACTCACTGCTTTTGATGTTTATTTGCGCTATAAAGAATTAT
ATGAGAATCAAAGAATTACATCTGGCGTATATATGTGTGCAGTTGCTATT
GCGATGGGATATACAGATATTTACTTAACTGGTATCGATTTTTATCAAGC
GAGCGAAGAAAACTACGCATTCGATAATAAAAAGCCTAACATTATTAGGT
TATTGCCTGATTTTCGGAAAGAAAAAACACTCTTTTCTTATCATAGTAAA
GATATTGATTTGGAAGCATTATCTTTTTTACAACAGCATTATCATGTTAA
TTTTTATTCAATTTCACCAATGAGCCCTTTGTCTAAACATTTTCCTATTC
CAACTGTAGAGGATGATTGTGAAACAACTTTTGTTGCGCCACTAAAAGAA
AATTACATTAATGATATATTGTTGCCTCCTCATTTTGTATATGAAAAATT
AGGGGTCGACAAGCTTGCGGCCGCACTCGAGCACCACCACCACCACCACT
GA (WTPmST3Δ45-His$_6$)

SEQ ID NO: 21

ATGGATAAGTTCGCAGAACATGAAATACCGAAAGCCGTTATTGTTGCAGG
GAATGGCGAGAGTTTAAGTCAAATTGATTATAGGTTGTTACCGAAAAATT
ATGATGTGTTTCGTTGTAATCAATTTTATTTTGAAGAACGCTATTTTTTA
GGAAACAAGATAAAAGCAGTTTTCTTCACGCCAGGGGTCTTTCTTGAGCA
ATATTATACACTTTATCATCTCAAGAGAAACAATGAGTATTTTGTTGATA
ATGTGATTCTCTCTTCTTTTAATCATCCTACAGTAGATTTAGAAAAGAGT

-continued

CAGAAAATACAAGCACTTTTTATTGATGTGATCAACGGATATGAAAAGTA
TTTATCTAAACTCACTGCTTTTGATGTTTATTTGCGCTATAAAGAATTAT
ATGAGAATCAAAGAATTACATCTGGCGTATATATGTGTGCAGTTGCTATT
GCGATGGGATATACAGATATTTACTTAACTGGTATCGATTTTTATCAAGC
GAGCGAAGAAAACTACGCATTCGATAATAAAAAGCCTAACATTATTAGGT
TATTGCCTGATTTTCGGAAAGAAAAAACACTCTTTTCTTATCATAGTAAA

-continued

GATATTGATTTGGAAGCATTATCTTTTTTACAACAGCATTATCATGTTAA
TTTTTATTCAATTTCACCAATGAGCCCTTTGTCTAAACATTTTCCTATTC
CAACTGTAGAGGATGATTGTGAAACAACTTTTGTTGCGCCACTAAAAGAA
AATTACATTAATGATATATTGTTGGTCGACAAGCTTGCGGCCGCACTCGA
GCACCACCACCACCACCATGA

What is claimed is:

1. A method of preparing a glycosylated molecule, the method comprising:

a) forming a reaction mixture comprising an acceptor molecule, a donor substrate, and the polypeptide according to SEQ ID NO:7, wherein the polypeptide lacks the C-terminal 35 amino acid residues of SEQ ID NO:7;

wherein the acceptor molecule is selected from the group consisting of an oligosaccharide, a polysaccharide, a glycopeptide, a glycoprotein, and a glycolipid;

wherein the donor substrate is selected from the group consisting of a cytidine 5'-monophosphate-sialic acid (CMP-sialic acid), an O-acetyl CMP-sialic acid, and an N-acetyl CMP-sialic acid; and wherein the reaction mixture is formed under conditions sufficient to transfer the sialic acid from the donor substrate to the acceptor molecule, thereby forming the glycosylated molecule.

2. The method of claim 1, wherein the acceptor molecule comprises a galactoside moiety.

3. The method of claim 2, wherein the galactoside moiety is selected from the group consisting of a β1-4 linked galactoside moiety and a β1-3 linked galactoside moiety.

4. The method of claim 1, wherein the acceptor molecule comprises a lactoside (LacβOR) or an N-acetyl lactosaminide (LacNAcβOR), wherein R represents the remainder of the acceptor molecule.

5. The method of claim 1, wherein the acceptor molecule comprises a lacto-N-bioside moiety or a galacto-N-bioside moiety.

6. The method of claim 1, wherein the CMP-sialic acid is selected from the group consisting of cytidine 5'-monophosphate N-acetylneuraminic acid (CMP-Neu5Ac), cytidine 5'-monophosphate N-glycolylneuraminic acid (CMP-Neu5Gc), an O-acetyl derivative thereof, or an N-acetyl derivative thereof.

7. The method of claim 6, further comprising:

b) forming a reaction mixture comprising a CMP-sialic acid synthetase; cytidine triphosphate; and Neu5Ac, Neu5Gc, an O-acetyl derivative thereof, or an N-acetyl derivative thereof;

wherein the reaction mixture is formed under conditions suitable to form the CMP-Neu5Ac, the CMP-Neu5Gc, the O-acetyl derivative thereof, or the N-acetyl derivative thereof.

8. The method of claim 7, wherein steps a) and b) are performed in one pot.

9. The method of claim 7, further comprising:

c) forming a reaction mixture comprising a sialic acid aldolase; pyruvic acid or thereof; and N-acetylmannosamine N-glycolylmannosamine, an O-acetyl derivative thereof, or an N-acetyl derivative thereof;

wherein the reaction mixture is formed under conditions sufficient to form the Neu5Ac, the Neu5Gc, the O-acetyl derivative thereof, or the N-acetyl derivative thereof.

10. The method of claim 9, wherein steps a), b), and c) are performed in one pot.

11. The method of claim 1, wherein the glycosylated molecule comprises an α2-3-linked sialic acid residue.

12. The method of claim 1, wherein the reaction mixture is formed in vitro.

13. The method of claim 1, wherein the polypeptide further comprises a tag sequence to facilitate purification.

14. The method of claim 13, wherein the polypeptide further comprising the tag sequence to facilitate purification has the amino acid sequence according to SEQ ID NO: 11.

15. A method of preparing a glycosylated molecule, the method comprising:

forming a reaction mixture comprising an acceptor molecule comprising a galactoside moiety; a donor substrate comprising a cytidine 5'-monophosphate-sialic acid (CMP-sialic acid); and the polypeptide according to SEQ ID NO:11;

wherein the reaction mixture is formed under conditions sufficient to transfer the sialic acid from the donor substrate to the galactoside moiety, thereby forming the glycosylated molecule.

16. The method of claim 15, wherein the acceptor molecule is selected from the group consisting of an oligosaccharide, a glycopeptide, a glycoprotein, and a glycolipid.

17. The method of claim 15, wherein the glycosylated molecule comprises an α2-3-linked sialic acid residue.

* * * * *

UNITED STATES PATENT AND TRADEMARK OFFICE

CERTIFICATE OF CORRECTION

PATENT NO. : 9,783,838 B2
APPLICATION NO. : 14/356376
DATED : October 10, 2017
INVENTOR(S) : Chen et al.

It is certified that error appears in the above-identified patent and that said Letters Patent is hereby corrected as shown below:

On the Title Page

Item (60), please delete "Nov. 7, 2012" and insert --Nov. 7, 2011--

In the Claims

In Claim 9, Column 73, Line 3, please delete "or thereof" and insert --;--

Signed and Sealed this
Thirteenth Day of March, 2018

Andrei Iancu
*Director of the United States Patent and Trademark Office*

SEQUENCE LISTING

<160> NUMBER OF SEQ ID NOS: 37

<210> SEQ ID NO 1
<211> LENGTH: 912
<212> TYPE: DNA
<213> ORGANISM: Pasteurella multocida
<220> FEATURE:
<223> OTHER INFORMATION: Pasteurella multocida sialyltransferase 3 (PmST3, Pm1174), sialidase-free monofunctional alpha2-3-sialyltransferase

<400> SEQUENCE: 1

```
atggataaat ttgccgaaca tgaaattccg aaagccgtta ttgttgcagg taatggtgaa     60

agcctgagcc agattgatta tcgtctgctg ccgaaaaatt atgatgtgtt tcgctgcaat    120

cagttttatt ttgaagaacg ctattttctg ggcaataaaa ttaaagccgt gtttttttaca    180

ccgggtgttt ttctggaaca gtattatacc ctgtatcatc tgaaacgcaa taatgaatat    240

tttgtggata atgtgattct gagcagcttt aatcatccga ccgttgatct ggaaaaaagc    300

cagaaaattc aggccctgtt tattgatgtg attaatggct atgaaaaata tctgagcaaa    360

ctgaccgcct ttgatgttta tctgcgctat aaagaactgt atgaaaatca gcgtattacc    420

agcggtgttt atatgtgtgc agttgcaatt gcaatgggct ataccgatat ttatctgacc    480

ggcattgatt tttatcaggc cagcgaagaa aattatgcct ttgataataa aaaaccgaat    540

attattcgcc tgctgccgga ttttcgcaaa gaaaaaaccc tgtttagcta tcatagcaaa    600

gatattgatc tggaagccct gagctttctg cagcagcatt atcatgtgaa tttttatagc    660

attagcccga tgagtccgct gagcaaacat tttccgattc cgaccgtgga agatgattgt    720

gaaaccacct ttgttgcacc gctgaaagaa aattatatta atgatattct gctgcctccg    780

cattttgtgt atgaaaaact gggcaccatt gtgagcaaaa aaagccgttt tcatagcaat    840

ctgattgtgc gtctgattcg tgatctgctg aaactgccga gcgcactgaa acattatctg    900

aaagaaaaat aa                                                         912
```

<210> SEQ ID NO 2
<211> LENGTH: 936
<212> TYPE: DNA
<213> ORGANISM: Artificial Sequence
<220> FEATURE:
<223> OTHER INFORMATION: synthetic Pasteurella multocida sialyltransferase 3 (PmST3, Pm1174) C-His-6 tagged fusion protein PmST3-His-6

<400> SEQUENCE: 2

```
atggataaat ttgccgaaca tgaaattccg aaagccgtta ttgttgcagg taatggtgaa     60

agcctgagcc agattgatta tcgtctgctg ccgaaaaatt atgatgtgtt tcgctgcaat    120

cagttttatt ttgaagaacg ctattttctg ggcaataaaa ttaaagccgt gtttttttaca    180

ccgggtgttt ttctggaaca gtattatacc ctgtatcatc tgaaacgcaa taatgaatat    240

tttgtggata atgtgattct gagcagcttt aatcatccga ccgttgatct ggaaaaaagc    300

cagaaaattc aggccctgtt tattgatgtg attaatggct atgaaaaata tctgagcaaa    360
```

-continued

```
ctgaccgcct ttgatgttta tctgcgctat aaagaactgt atgaaaatca gcgtattacc    420

agcggtgttt atatgtgtgc agttgcaatt gcaatgggct ataccgatat ttatctgacc    480

ggcattgatt tttatcaggc cagcgaagaa aattatgcct ttgataataa aaaaccgaat    540

attattcgcc tgctgccgga ttttcgcaaa gaaaaaaccc tgtttagcta tcatagcaaa    600

gatattgatc tggaagccct gagctttctg cagcagcatt atcatgtgaa tttttatagc    660

attagcccga tgagtccgct gagcaaacat tttccgattc cgaccgtgga agatgattgt    720

gaaaccacct ttgttgcacc gctgaaagaa aattatatta atgatattct gctgcctccg    780

cattttgtgt atgaaaaact gggcaccatt gtgagcaaaa aaagccgttt tcatagcaat    840

ctgattgtgc gtctgattcg tgatctgctg aaactgccga gcgcactgaa acattatctg    900

aaagaaaaac tcgagcacca ccaccaccac cactga                              936
```

<210> SEQ ID NO 3
<211> LENGTH: 2103
<212> TYPE: DNA
<213> ORGANISM: Artificial Sequence
<220> FEATURE:
<223> OTHER INFORMATION: synthetic maltose binding protein Pasteurella multocida sialyltransferase 3 (PmST3, Pm1174) C-His-6 tagged fusion protein MBP-PmST3-His-6

<400> SEQUENCE: 3

```
atgaaaatcg aagaaggtaa actggtaatc tggattaacg gcgataaagg ctataacggt     60

ctcgctgaag tcggtaagaa attcgagaaa gataccggaa ttaaagtcac cgttgagcat    120

ccggataaac tggaagagaa attcccacag gttgcggcaa ctggcgatgg ccctgacatt    180

atcttctggg cacacgaccg ctttggtggc tacgctcaat ctggcctgtt ggctgaaatc    240

accccggaca aagcgttcca ggacaagctg tatccgttta cctgggatgc cgtacgttac    300

aacggcaagc tgattgctta cccgatcgct gttgaagcgt tatcgctgat ttataacaaa    360

gatctgctgc cgaacccgcc aaaaacctgg gaagagatcc cggcgctgga taaagaactg    420

aaagcgaaag gtaagagcgc gctgatgttc aacctgcaag aaccgtactt cacctggccg    480

ctgattgctg ctgacggggg ttatgcgttc aagtatgaaa acggcaagta cgacattaaa    540

gacgtgggcg tggataacgc tggcgcgaaa gcgggtctga ccttcctggt tgacctgatt    600

aaaaacaaac acatgaatgc agacaccgat tactccatcg cagaagctgc ctttaataaa    660

ggcgaaacag cgatgaccat caacggcccg tgggcatggt ccaacatcga caccagcaaa    720

gtgaattatg gtgtaacggt actgccgacc ttcaagggtc aaccatccaa accgttcgtt    780

ggcgtgctga gcgcaggtat taacgccgcc agtccgaaca aagagctggc aaaagagttc    840

ctcgaaaact atctgctgac tgatgaaggt ctggaagcgg ttaataaaga caaaccgctg    900

ggtgccgtag cgctgaagtc ttacgaggaa gagttggtga aagatccgcg gattgccgcc    960

actatggaaa acgcccagaa aggtgaaatc atgccgaaca tcccgcagat gtccgctttc   1020

tggtatgccg tgcgtactgc ggtgatcaac gccgccagcg gtcgtcagac tgtcgatgaa   1080

gccctgaaag acgcgcagac taattcgagc tcgaacaaca acaacaataa caataacaac   1140

aacctcggga tcgagggaag gatttcagaa ttcatggata aatttgccga acatgaaatt   1200

ccgaaagccg ttattgttgc aggtaatggt gaaagcctga gccagattga ttatcgtctg   1260

ctgccgaaaa attatgatgt gtttcgctgc aatcagtttt attttgaaga acgctatttt   1320

ctgggcaata aaattaaagc cgtgtttttt acaccgggtg tttttctgga acagtattat   1380
```

-continued accctgtatc atctgaaacg caataatgaa tattttgtgg ataatgtgat tctgagcagc 1440
tttaatcatc cgaccgttga tctggaaaaa agccagaaaa ttcaggccct gtttattgat 1500
gtgattaatg gctatgaaaa atatctgagc aaactgaccg cctttgatgt ttatctgcgc 1560
tataaagaac tgtatgaaaa tcagcgtatt accagcggtg tttatatgtg tgcagttgca 1620
attgcaatgg gctataccga tatttatctg accggcattg atttttatca ggccagcgaa 1680
gaaaattatg cctttgataa taaaaaaccg aatattattc gcctgctgcc ggattttcgc 1740
aaagaaaaaa ccctgtttag ctatcatagc aaagatattg atctggaagc cctgagcttt 1800
ctgcagcagc attatcatgt gaatttttat agcattagcc cgatgagtcc gctgagcaaa 1860
cattttccga ttccgaccgt ggaagatgat tgtgaaacca cctttgttgc accgctgaaa 1920
gaaaattata ttaatgatat tctgctgcct ccgcattttg tgtatgaaaa actgggcacc 1980
attgtgagca aaaaaagccg ttttcatagc aatctgattg tgcgtctgat tcgtgatctg 2040
ctgaaactgc cgagcgcact gaaacattat ctgaaagaaa aacaccacca ccaccaccac 2100
taa 2103

<210> SEQ ID NO 4
<211> LENGTH: 897
<212> TYPE: DNA
<213> ORGANISM: Artificial Sequence
<220> FEATURE:
<223> OTHER INFORMATION: synthetic C-terminal truncated Pasteurella multocida sialyltransferase 3 (PmST3, Pm1174) C-His-6 tagged fusion protein PmST3delta20-His-6

<400> SEQUENCE: 4
atggataaat ttgccgaaca tgaaattccg aaagccgtta ttgttgcagg taatggtgaa 60
agcctgagcc agattgatta tcgtctgctg ccgaaaaatt atgatgtgtt tcgctgcaat 120
cagttttatt ttgaagaacg ctatttttctg ggcaataaaa ttaaagccgt gtttttttaca 180 ccgggtgttt ttctggaaca gtattatacc ctgtatcatc tgaaacgcaa taatgaatat 240
tttgtggata atgtgattct gagcagcttt aatcatccga ccgttgatct ggaaaaaagc 300
cagaaaattc aggccctgtt tattgatgtg attaatggct atgaaaaata tctgagcaaa 360
ctgaccgcct ttgatgttta tctgcgctat aaagaactgt atgaaaatca gcgtattacc 420
agcggtgttt atatgtgtgc agttgcaatt gcaatgggct ataccgatat ttatctgacc 480
ggcattgatt tttatcaggc cagcgaagaa aattatgcct ttgataataa aaaaccgaat 540
attattcgcc tgctgccgga ttttcgcaaa gaaaaaaccc tgtttagcta tcatagcaaa 600
gatattgatc tggaagccct gagctttctg cagcagcatt atcatgtgaa tttttatagc 660
attagcccga tgagtccgct gagcaaacat tttccgattc cgaccgtgga agatgattgt 720
gaaaccacct ttgttgcacc gctgaaagaa aattatatta atgatattct gctgcctccg 780
cattttgtgt atgaaaaact gggcaccatt gtgagcaaaa aaagccgttt tcatagcaat 840
ctgattgtgg tcgacaagct tgcggccgca ctcgagcacc accaccacca ccactga 897

<210> SEQ ID NO 5
<211> LENGTH: 852
<212> TYPE: DNA
<213> ORGANISM: Artificial Sequence
<220> FEATURE:
<223> OTHER INFORMATION: synthetic C-terminal truncated Pasteurella multocida sialyltransferase 3 (PmST3, Pm1174) C-His-6 tagged fusion protein PmST3delta35-His-6

<400> SEQUENCE: 5

-continued atggataaat ttgccgaaca tgaaattccg aaagccgtta ttgttgcagg taatggtgaa 60
agcctgagcc agattgatta tcgtctgctg ccgaaaaatt atgatgtgtt tcgctgcaat 120
cagttttatt ttgaagaacg ctattttctg ggcaataaaa ttaaagccgt gttttttaca 180
ccgggtgttt ttctggaaca gtattatacc ctgtatcatc tgaaacgcaa taatgaatat 240
tttgtggata atgtgattct gagcagcttt aatcatccga ccgttgatct ggaaaaaagc 300
cagaaaattc aggccctgtt tattgatgtg attaatggct atgaaaaata tctgagcaaa 360
ctgaccgcct ttgatgttta tctgcgctat aaagaactgt atgaaaatca gcgtattacc 420
agcggtgttt atatgtgtgc agttgcaatt gcaatgggct ataccgatat ttatctgacc 480
ggcattgatt tttatcaggc cagcgaagaa aattatgcct ttgataataa aaaaccgaat 540
attattcgcc tgctgccgga ttttcgcaaa gaaaaaaccc tgtttagcta tcatagcaaa 600
gatattgatc tggaagccct gagctttctg cagcagcatt atcatgtgaa tttttatagc 660
attagcccga tgagtccgct gagcaaacat tttccgattc cgaccgtgga agatgattgt 720
gaaaccacct ttgttgcacc gctgaaagaa aattatatta atgatattct gctgcctccg 780
cattttgtgt atgaaaaact gggcgtcgac aagcttgcgg ccgcactcga gcaccaccac 840
caccaccact ga 852

<210> SEQ ID NO 6
<211> LENGTH: 822
<212> TYPE: DNA
<213> ORGANISM: Artificial Sequence
<220> FEATURE:
<223> OTHER INFORMATION: synthetic C-terminal truncated Pasteurella multocida sialyltransferase 3 (PmST3, Pm1174) C-His-6 tagged fusion protein PmST3delta45-His-6

<400> SEQUENCE: 6
atggataaat ttgccgaaca tgaaattccg aaagccgtta ttgttgcagg taatggtgaa 60
agcctgagcc agattgatta tcgtctgctg ccgaaaaatt atgatgtgtt tcgctgcaat 120
cagttttatt ttgaagaacg ctattttctg ggcaataaaa ttaaagccgt gttttttaca 180
ccgggtgttt ttctggaaca gtattatacc ctgtatcatc tgaaacgcaa taatgaatat 240
tttgtggata atgtgattct gagcagcttt aatcatccga ccgttgatct ggaaaaaagc 300
cagaaaattc aggccctgtt tattgatgtg attaatggct atgaaaaata tctgagcaaa 360
ctgaccgcct ttgatgttta tctgcgctat aaagaactgt atgaaaatca gcgtattacc 420
agcggtgttt atatgtgtgc agttgcaatt gcaatgggct ataccgatat ttatctgacc 480
ggcattgatt tttatcaggc cagcgaagaa aattatgcct ttgataataa aaaaccgaat 540
attattcgcc tgctgccgga ttttcgcaaa gaaaaaaccc tgtttagcta tcatagcaaa 600
gatattgatc tggaagccct gagctttctg cagcagcatt atcatgtgaa tttttatagc 660
attagcccga tgagtccgct gagcaaacat tttccgattc cgaccgtgga agatgattgt 720
gaaaccacct ttgttgcacc gctgaaagaa aattatatta atgatattct gctggtcgac 780
aagcttgcgg ccgcactcga gcaccaccac caccaccact ga 822

<210> SEQ ID NO 7
<211> LENGTH: 303
<212> TYPE: PRT
<213> ORGANISM: Pasteurella multocida
<220> FEATURE:
<223> OTHER INFORMATION: Pasteurella multocida sialyltransferase 3 (PmST3, Pm1174), sialidase-free monofunctional alpha2-3- sialyltransferase

<400> SEQUENCE: 7

Met Asp Lys Phe Ala Glu His Glu Ile Pro Lys Ala Val Ile Val Ala
1 5 10 15

Gly Asn Gly Glu Ser Leu Ser Gln Ile Asp Tyr Arg Leu Leu Pro Lys
20 25 30

Asn Tyr Asp Val Phe Arg Cys Asn Gln Phe Tyr Phe Glu Glu Arg Tyr
35 40 45

Phe Leu Gly Asn Lys Ile Lys Ala Val Phe Phe Thr Pro Gly Val Phe
50 55 60

Leu Glu Gln Tyr Tyr Thr Leu Tyr His Leu Lys Arg Asn Asn Glu Tyr
65 70 75 80

Phe Val Asp Asn Val Ile Leu Ser Ser Phe Asn His Pro Thr Val Asp
85 90 95

Leu Glu Lys Ser Gln Lys Ile Gln Ala Leu Phe Ile Asp Val Ile Asn
100 105 110

Gly Tyr Glu Lys Tyr Leu Ser Lys Leu Thr Ala Phe Asp Val Tyr Leu
115 120 125

Arg Tyr Lys Glu Leu Tyr Glu Asn Gln Arg Ile Thr Ser Gly Val Tyr
130 135 140

Met Cys Ala Val Ala Ile Ala Met Gly Tyr Thr Asp Ile Tyr Leu Thr
145 150 155 160

Gly Ile Asp Phe Tyr Gln Ala Ser Glu Glu Asn Tyr Ala Phe Asp Asn
165 170 175

Lys Lys Pro Asn Ile Ile Arg Leu Leu Pro Asp Phe Arg Lys Glu Lys
180 185 190

Thr Leu Phe Ser Tyr His Ser Lys Asp Ile Asp Leu Glu Ala Leu Ser
195 200 205

Phe Leu Gln Gln His Tyr His Val Asn Phe Tyr Ser Ile Ser Pro Met
210 215 220

Ser Pro Leu Ser Lys His Phe Pro Ile Pro Thr Val Glu Asp Asp Cys
225 230 235 240

Glu Thr Thr Phe Val Ala Pro Leu Lys Glu Asn Tyr Ile Asn Asp Ile
245 250 255

Leu Leu Pro Pro His Phe Val Tyr Glu Lys Leu Gly Thr Ile Val Ser
260 265 270

Lys Lys Ser Arg Phe His Ser Asn Leu Ile Val Arg Leu Ile Arg Asp
275 280 285

Leu Leu Lys Leu Pro Ser Ala Leu Lys His Tyr Leu Lys Glu Lys
290 295 300

<210> SEQ ID NO 8
<211> LENGTH: 311
<212> TYPE: PRT
<213> ORGANISM: Artificial Sequence
<220> FEATURE:
<223> OTHER INFORMATION: synthetic Pateurella multocida sialyltransferase 3 (PmST3, Pm1174) C-His-6 tagged fusion protein PmST3-His-6

<400> SEQUENCE: 8

Met Asp Lys Phe Ala Glu His Glu Ile Pro Lys Ala Val Ile Val Ala
1 5 10 15

Gly Asn Gly Glu Ser Leu Ser Gln Ile Asp Tyr Arg Leu Leu Pro Lys
20 25 30

```
Asn Tyr Asp Val Phe Arg Cys Asn Gln Phe Tyr Phe Glu Glu Arg Tyr
        35                  40                  45

Phe Leu Gly Asn Lys Ile Lys Ala Val Phe Phe Thr Pro Gly Val Phe
    50                  55                  60

Leu Glu Gln Tyr Tyr Thr Leu Tyr His Leu Lys Arg Asn Asn Glu Tyr
65                  70                  75                  80

Phe Val Asp Asn Val Ile Leu Ser Ser Phe Asn His Pro Thr Val Asp
                85                  90                  95

Leu Glu Lys Ser Gln Lys Ile Gln Ala Leu Phe Ile Asp Val Ile Asn
            100                 105                 110

Gly Tyr Glu Lys Tyr Leu Ser Lys Leu Thr Ala Phe Asp Val Tyr Leu
        115                 120                 125

Arg Tyr Lys Glu Leu Tyr Glu Asn Gln Arg Ile Thr Ser Gly Val Tyr
    130                 135                 140

Met Cys Ala Val Ala Ile Ala Met Gly Tyr Thr Asp Ile Tyr Leu Thr
145                 150                 155                 160

Gly Ile Asp Phe Tyr Gln Ala Ser Glu Glu Asn Tyr Ala Phe Asp Asn
                165                 170                 175

Lys Lys Pro Asn Ile Ile Arg Leu Leu Pro Asp Phe Arg Lys Glu Lys
            180                 185                 190

Thr Leu Phe Ser Tyr His Ser Lys Asp Ile Asp Leu Glu Ala Leu Ser
        195                 200                 205

Phe Leu Gln Gln His Tyr His Val Asn Phe Tyr Ser Ile Ser Pro Met
    210                 215                 220

Ser Pro Leu Ser Lys His Phe Pro Ile Pro Thr Val Glu Asp Asp Cys
225                 230                 235                 240

Glu Thr Thr Phe Val Ala Pro Leu Lys Glu Asn Tyr Ile Asn Asp Ile
                245                 250                 255

Leu Leu Pro Pro His Phe Val Tyr Glu Lys Leu Gly Thr Ile Val Ser
            260                 265                 270

Lys Lys Ser Arg Phe His Ser Asn Leu Ile Val Arg Leu Ile Arg Asp
        275                 280                 285

Leu Leu Lys Leu Pro Ser Ala Leu Lys His Tyr Leu Lys Glu Lys Leu
    290                 295                 300

Glu His His His His His His
305                 310


<210> SEQ ID NO 9
<211> LENGTH: 700
<212> TYPE: PRT
<213> ORGANISM: Artificial Sequence
<220> FEATURE:
<223> OTHER INFORMATION: synthetic maltose binding protein Pasteurella
      multocida sialyltransferase 3 (PmST3, Pm1174) C-His-6 tagged
      fusion protein MBP-PmST3-His-6

<400> SEQUENCE: 9

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
```

-continued

```
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380

Glu Gly Arg Ile Ser Glu Phe Met Asp Lys Phe Ala Glu His Glu Ile
385                 390                 395                 400

Pro Lys Ala Val Ile Val Ala Gly Asn Gly Glu Ser Leu Ser Gln Ile
                405                 410                 415

Asp Tyr Arg Leu Leu Pro Lys Asn Tyr Asp Val Phe Arg Cys Asn Gln
            420                 425                 430

Phe Tyr Phe Glu Glu Arg Tyr Phe Leu Gly Asn Lys Ile Lys Ala Val
        435                 440                 445

Phe Phe Thr Pro Gly Val Phe Leu Glu Gln Tyr Tyr Thr Leu Tyr His
    450                 455                 460

Leu Lys Arg Asn Asn Glu Tyr Phe Val Asp Asn Val Ile Leu Ser Ser
465                 470                 475                 480

Phe Asn His Pro Thr Val Asp Leu Glu Lys Ser Gln Lys Ile Gln Ala
                485                 490                 495
```

```
Leu Phe Ile Asp Val Ile Asn Gly Tyr Glu Lys Tyr Leu Ser Lys Leu
            500                 505                 510

Thr Ala Phe Asp Val Tyr Leu Arg Tyr Lys Glu Leu Tyr Glu Asn Gln
        515                 520                 525

Arg Ile Thr Ser Gly Val Tyr Met Cys Ala Val Ala Ile Ala Met Gly
    530                 535                 540

Tyr Thr Asp Ile Tyr Leu Thr Gly Ile Asp Phe Tyr Gln Ala Ser Glu
545                 550                 555                 560

Glu Asn Tyr Ala Phe Asp Asn Lys Lys Pro Asn Ile Ile Arg Leu Leu
                565                 570                 575

Pro Asp Phe Arg Lys Glu Lys Thr Leu Phe Ser Tyr His Ser Lys Asp
            580                 585                 590

Ile Asp Leu Glu Ala Leu Ser Phe Leu Gln Gln His Tyr His Val Asn
        595                 600                 605

Phe Tyr Ser Ile Ser Pro Met Ser Pro Leu Ser Lys His Phe Pro Ile
    610                 615                 620

Pro Thr Val Glu Asp Asp Cys Glu Thr Thr Phe Val Ala Pro Leu Lys
625                 630                 635                 640

Glu Asn Tyr Ile Asn Asp Ile Leu Leu Pro Pro His Phe Val Tyr Glu
                645                 650                 655

Lys Leu Gly Thr Ile Val Ser Lys Lys Ser Arg Phe His Ser Asn Leu
            660                 665                 670

Ile Val Arg Leu Ile Arg Asp Leu Leu Lys Leu Pro Ser Ala Leu Lys
        675                 680                 685

His Tyr Leu Lys Glu Lys His His His His His His
    690                 695                 700


<210> SEQ ID NO 10
<211> LENGTH: 298
<212> TYPE: PRT
<213> ORGANISM: Artificial Sequence
<220> FEATURE:
<223> OTHER INFORMATION: synthetic C-terminal truncated Pasteurella
      multocida sialyltransferase 3 (PmST3, Pm1174) C-His-6 tagged
      fusion protein PmST3delta20-His-6

<400> SEQUENCE: 10

Met Asp Lys Phe Ala Glu His Glu Ile Pro Lys Ala Val Ile Val Ala
 1               5                  10                  15

Gly Asn Gly Glu Ser Leu Ser Gln Ile Asp Tyr Arg Leu Leu Pro Lys
            20                  25                  30

Asn Tyr Asp Val Phe Arg Cys Asn Gln Phe Tyr Phe Glu Glu Arg Tyr
        35                  40                  45

Phe Leu Gly Asn Lys Ile Lys Ala Val Phe Phe Thr Pro Gly Val Phe
    50                  55                  60

Leu Glu Gln Tyr Tyr Thr Leu Tyr His Leu Lys Arg Asn Asn Glu Tyr
65                  70                  75                  80

Phe Val Asp Asn Val Ile Leu Ser Ser Phe Asn His Pro Thr Val Asp
                85                  90                  95

Leu Glu Lys Ser Gln Lys Ile Gln Ala Leu Phe Ile Asp Val Ile Asn
            100                 105                 110

Gly Tyr Glu Lys Tyr Leu Ser Lys Leu Thr Ala Phe Asp Val Tyr Leu
        115                 120                 125

Arg Tyr Lys Glu Leu Tyr Glu Asn Gln Arg Ile Thr Ser Gly Val Tyr
    130                 135                 140
```

Met Cys Ala Val Ala Ile Ala Met Gly Tyr Thr Asp Ile Tyr Leu Thr
145 150 155 160

Gly Ile Asp Phe Tyr Gln Ala Ser Glu Glu Asn Tyr Ala Phe Asp Asn
165 170 175

Lys Lys Pro Asn Ile Ile Arg Leu Leu Pro Asp Phe Arg Lys Glu Lys
180 185 190

Thr Leu Phe Ser Tyr His Ser Lys Asp Ile Asp Leu Glu Ala Leu Ser
195 200 205

Phe Leu Gln Gln His Tyr His Val Asn Phe Tyr Ser Ile Ser Pro Met
210 215 220

Ser Pro Leu Ser Lys His Phe Pro Ile Pro Thr Val Glu Asp Asp Cys
225 230 235 240

Glu Thr Thr Phe Val Ala Pro Leu Lys Glu Asn Tyr Ile Asn Asp Ile
245 250 255

Leu Leu Pro Pro His Phe Val Tyr Glu Lys Leu Gly Thr Ile Val Ser
260 265 270

Lys Lys Ser Arg Phe His Ser Asn Leu Ile Val Val Asp Lys Leu Ala
275 280 285

Ala Ala Leu Glu His His His His His His
290 295

<210> SEQ ID NO 11
<211> LENGTH: 283
<212> TYPE: PRT
<213> ORGANISM: Artificial Sequence
<220> FEATURE:
<223> OTHER INFORMATION: synthetic C-terminal truncated Pasteurella multocida sialyltransferase 3 (PmST3, Pm1174) C-His-6 tagged fusion protein PmST3delta35-His-6

<400> SEQUENCE: 11

Met Asp Lys Phe Ala Glu His Glu Ile Pro Lys Ala Val Ile Val Ala
1 5 10 15

Gly Asn Gly Glu Ser Leu Ser Gln Ile Asp Tyr Arg Leu Leu Pro Lys
20 25 30

Asn Tyr Asp Val Phe Arg Cys Asn Gln Phe Tyr Phe Glu Glu Arg Tyr
35 40 45

Phe Leu Gly Asn Lys Ile Lys Ala Val Phe Phe Thr Pro Gly Val Phe
50 55 60

Leu Glu Gln Tyr Tyr Thr Leu Tyr His Leu Lys Arg Asn Asn Glu Tyr
65 70 75 80

Phe Val Asp Asn Val Ile Leu Ser Ser Phe Asn His Pro Thr Val Asp
85 90 95

Leu Glu Lys Ser Gln Lys Ile Gln Ala Leu Phe Ile Asp Val Ile Asn
100 105 110

Gly Tyr Glu Lys Tyr Leu Ser Lys Leu Thr Ala Phe Asp Val Tyr Leu
115 120 125

Arg Tyr Lys Glu Leu Tyr Glu Asn Gln Arg Ile Thr Ser Gly Val Tyr
130 135 140

Met Cys Ala Val Ala Ile Ala Met Gly Tyr Thr Asp Ile Tyr Leu Thr
145 150 155 160

Gly Ile Asp Phe Tyr Gln Ala Ser Glu Glu Asn Tyr Ala Phe Asp Asn
165 170 175

Lys Lys Pro Asn Ile Ile Arg Leu Leu Pro Asp Phe Arg Lys Glu Lys
180 185 190

Thr Leu Phe Ser Tyr His Ser Lys Asp Ile Asp Leu Glu Ala Leu Ser

-continued

```
        195                 200                 205

Phe Leu Gln Gln His Tyr His Val Asn Phe Tyr Ser Ile Ser Pro Met
    210                 215                 220

Ser Pro Leu Ser Lys His Phe Pro Ile Pro Thr Val Glu Asp Asp Cys
225                 230                 235                 240

Glu Thr Thr Phe Val Ala Pro Leu Lys Glu Asn Tyr Ile Asn Asp Ile
                245                 250                 255

Leu Leu Pro Pro His Phe Val Tyr Glu Lys Leu Gly Val Asp Lys Leu
            260                 265                 270

Ala Ala Ala Leu Glu His His His His His His
        275                 280


<210> SEQ ID NO 12
<211> LENGTH: 273
<212> TYPE: PRT
<213> ORGANISM: Artificial Sequence
<220> FEATURE:
<223> OTHER INFORMATION: synthetic C-terminal truncated Pasteurella
      multocida sialyltransferase 3 (PmST3, Pm1174) C-His-6 tagged
      fusion protein PmST3delta45-His-6

<400> SEQUENCE: 12

Met Asp Lys Phe Ala Glu His Glu Ile Pro Lys Ala Val Ile Val Ala
 1               5                  10                  15

Gly Asn Gly Glu Ser Leu Ser Gln Ile Asp Tyr Arg Leu Leu Pro Lys
            20                  25                  30

Asn Tyr Asp Val Phe Arg Cys Asn Gln Phe Tyr Phe Glu Glu Arg Tyr
        35                  40                  45

Phe Leu Gly Asn Lys Ile Lys Ala Val Phe Phe Thr Pro Gly Val Phe
    50                  55                  60

Leu Glu Gln Tyr Tyr Thr Leu Tyr His Leu Lys Arg Asn Asn Glu Tyr
65                  70                  75                  80

Phe Val Asp Asn Val Ile Leu Ser Ser Phe Asn His Pro Thr Val Asp
                85                  90                  95

Leu Glu Lys Ser Gln Lys Ile Gln Ala Leu Phe Ile Asp Val Ile Asn
            100                 105                 110

Gly Tyr Glu Lys Tyr Leu Ser Lys Leu Thr Ala Phe Asp Val Tyr Leu
        115                 120                 125

Arg Tyr Lys Glu Leu Tyr Glu Asn Gln Arg Ile Thr Ser Gly Val Tyr
    130                 135                 140

Met Cys Ala Val Ala Ile Ala Met Gly Tyr Thr Asp Ile Tyr Leu Thr
145                 150                 155                 160

Gly Ile Asp Phe Tyr Gln Ala Ser Glu Glu Asn Tyr Ala Phe Asp Asn
                165                 170                 175

Lys Lys Pro Asn Ile Ile Arg Leu Leu Pro Asp Phe Arg Lys Glu Lys
            180                 185                 190

Thr Leu Phe Ser Tyr His Ser Lys Asp Ile Asp Leu Glu Ala Leu Ser
        195                 200                 205

Phe Leu Gln Gln His Tyr His Val Asn Phe Tyr Ser Ile Ser Pro Met
    210                 215                 220

Ser Pro Leu Ser Lys His Phe Pro Ile Pro Thr Val Glu Asp Asp Cys
225                 230                 235                 240

Glu Thr Thr Phe Val Ala Pro Leu Lys Glu Asn Tyr Ile Asn Asp Ile
                245                 250                 255

Leu Leu Val Asp Lys Leu Ala Ala Ala Leu Glu His His His His His
            260                 265                 270
```

His

<210> SEQ ID NO 13
<211> LENGTH: 6
<212> TYPE: PRT
<213> ORGANISM: Artificial Sequence
<220> FEATURE:
<223> OTHER INFORMATION: synthetic sialyltransferase motif A

<400> SEQUENCE: 13

Gly Ile Asp Phe Tyr Gln
1 5

<210> SEQ ID NO 14
<211> LENGTH: 3
<212> TYPE: PRT
<213> ORGANISM: Artificial Sequence
<220> FEATURE:
<223> OTHER INFORMATION: synthetic sialyltransferase motif B
<220> FEATURE:
<221> NAME/KEY: VARIANT
<222> LOCATION: (2)...(2)
<223> OTHER INFORMATION: Xaa = Ala or Pro

<400> SEQUENCE: 14

Tyr Xaa Phe
1

<210> SEQ ID NO 15
<211> LENGTH: 2
<212> TYPE: PRT
<213> ORGANISM: Artificial Sequence
<220> FEATURE:
<223> OTHER INFORMATION: synthetic sialyltransferase motif C

<400> SEQUENCE: 15

His Ser
1

<210> SEQ ID NO 16
<211> LENGTH: 912
<212> TYPE: DNA
<213> ORGANISM: Artificial Sequence
<220> FEATURE:
<223> OTHER INFORMATION: synthetic WTPmST3 sialyltransferase

<400> SEQUENCE: 16
atggataagt tcgcagaaca tgaaataccg aaagccgtta ttgttgcagg gaatggcgag 60
agtttaagtc aaattgatta taggttgtta ccgaaaaatt atgatgtgtt tcgttgtaat 120
caattttatt ttgaagaacg ctatttttta ggaaacaaga taaaagcagt tttcttcacg 180
ccaggggtct ttcttgagca atattataca ctttatcatc tcaagagaaa caatgagtat 240
tttgttgata atgtgattct ctcttctttt aatcatccta cagtagattt agaaaagagt 300
cagaaaatac aagcactttt tattgatgtg atcaacggat atgaaaagta tttatctaaa 360
ctcactgctt ttgatgttta tttgcgctat aaagaattat atgagaatca aagaattaca 420
tctggcgtat atatgtgtgc agttgctatt gcgatgggat atacagatat ttacttaact 480
ggtatcgatt tttatcaagc gagcgaagaa aactacgcat tcgataataa aaagcctaac 540
attattaggt tattgcctga ttttcggaaa gaaaaaacac tcttttctta tcatagtaaa 600
gatattgatt tggaagcatt atctttttta caacagcatt atcatgttaa tttttattca 660
atttcaccaa tgagcccttt gtctaaacat tttcctattc caactgtaga ggatgattgt 720
gaaacaactt ttgttgcgcc actaaaagaa aattacatta atgatatatt gttgcctcct 780
cattttgtat atgaaaaatt agggaccatc gtgtctaaga aatcacgttt tcattctaac 840
ttgattgtca ggttgattag agacttattg aaattaccga gtgcacttaa acactattta 900
aaagaaaaat ag 912

<210> SEQ ID NO 17
<211> LENGTH: 936
<212> TYPE: DNA
<213> ORGANISM: Artificial Sequence
<220> FEATURE:
<223> OTHER INFORMATION: synthetic WTPmST3-His-6 sialyltransferase fusion protein

<400> SEQUENCE: 17
atggataagt tcgcagaaca tgaaataccg aaagccgtta ttgttgcagg gaatggcgag 60
agtttaagtc aaattgatta taggttgtta ccgaaaaatt atgatgtgtt tcgttgtaat 120
caattttatt ttgaagaacg ctattttta ggaaacaaga taaaagcagt tttcttcacg 180
ccaggggtct ttcttgagca atattataca ctttatcatc tcaagagaaa caatgagtat 240
tttgttgata atgtgattct ctcttctttt aatcatccta cagtagattt agaaaagagt 300
cagaaaatac aagcactttt tattgatgtg atcaacggat atgaaaagta tttatctaaa 360
ctcactgctt ttgatgttta tttgcgctat aaagaattat atgagaatca aagaattaca 420
tctggcgtat atatgtgtgc agttgctatt gcgatgggat atacagatat ttacttaact 480
ggtatcgatt tttatcaagc gagcgaagaa aactacgcat tcgataataa aaagcctaac 540
attattaggt tattgcctga ttttcggaaa gaaaaaacac tcttttctta tcatagtaaa 600
gatattgatt tggaagcatt atctttttta caacagcatt atcatgttaa tttttattca 660
atttcaccaa tgagcccttt gtctaaacat tttcctattc caactgtaga ggatgattgt 720
gaaacaactt ttgttgcgcc actaaaagaa aattacatta atgatatatt gttgcctcct 780
cattttgtat atgaaaaatt agggaccatc gtgtctaaga aatcacgttt tcattctaac 840
ttgattgtca ggttgattag agacttattg aaattaccga gtgcacttaa acactattta 900
aaagaaaaac tcgagcacca ccaccaccac cactga 936

<210> SEQ ID NO 18
<211> LENGTH: 2103
<212> TYPE: DNA
<213> ORGANISM: Artificial Sequence
<220> FEATURE:
<223> OTHER INFORMATION: synthetic MBP-WTPmST3-His-6 sialyltransferase fusion protein

<400> SEQUENCE: 18
atgaaaatcg aagaaggtaa actggtaatc tggattaacg gcgataaagg ctataacggt 60
ctcgctgaag tcggtaagaa attcgagaaa gataccggaa ttaaagtcac cgttgagcat 120
ccggataaac tggaagagaa attcccacag gttgcggcaa ctggcgatgg ccctgacatt 180
atcttctggg cacacgaccg ctttggtggc tacgctcaat ctggcctgtt ggctgaaatc 240
accccggaca aagcgttcca ggacaagctg tatccgttta cctgggatgc cgtacgttac 300
aacggcaagc tgattgctta cccgatcgct gttgaagcgt tatcgctgat ttataacaaa 360
gatctgctgc cgaacccgcc aaaaacctgg gaagagatcc cggcgctgga taaagaactg 420
aaagcgaaag gtaagagcgc gctgatgttc aacctgcaag aaccgtactt cacctggccg 480

-continued

```
ctgattgctg ctgacggggg ttatgcgttc aagtatgaaa acggcaagta cgacattaaa    540

gacgtgggcg tggataacgc tggcgcgaaa gcgggtctga ccttcctggt tgacctgatt    600

aaaaacaaac acatgaatgc agacaccgat tactccatcg cagaagctgc ctttaataaa    660

ggcgaaacag cgatgaccat caacggcccg tgggcatggt ccaacatcga caccagcaaa    720

gtgaattatg gtgtaacggt actgccgacc ttcaagggtc aaccatccaa accgttcgtt    780

ggcgtgctga gcgcaggtat taacgccgcc agtccgaaca aagagctggc aaaagagttc    840

ctcgaaaact atctgctgac tgatgaaggt ctggaagcgg ttaataaaga caaaccgctg    900

ggtgccgtag cgctgaagtc ttacgaggaa gagttggtga aagatccgcg gattgccgcc    960

actatggaaa acgcccagaa aggtgaaatc atgccgaaca tcccgcagat gtccgctttc   1020

tggtatgccg tgcgtactgc ggtgatcaac gccgccagcg gtcgtcagac tgtcgatgaa   1080

gccctgaaag acgcgcagac taattcgagc tcgaacaaca acaacaataa caataacaac   1140

aacctcggga tcgagggaag gatttcagaa ttcatggata agttcgcaga acatgaaata   1200

ccgaaagccg ttattgttgc agggaatggc gagagtttaa gtcaaattga ttataggttg   1260

ttaccgaaaa attatgatgt gtttcgttgt aatcaatttt attttgaaga acgctatttt   1320

ttaggaaaca agataaaagc agttttcttc acgccagggg tctttcttga gcaatattat   1380

acactttatc atctcaagag aaacaatgag tattttgttg ataatgtgat tctctcttct   1440

tttaatcatc ctacagtaga tttagaaaag agtcagaaaa tacaagcact tttattgat   1500

gtgatcaacg gatatgaaaa gtatttatct aaactcactg cttttgatgt ttatttgcgc   1560

tataaagaat tatatgagaa tcaaagaatt acatctggcg tatatatgtg tgcagttgct   1620

attgcgatgg gatatacaga tatttactta actggtatcg atttttatca agcgagcgaa   1680

gaaaactacg cattcgataa taaaaagcct aacattatta ggttattgcc tgattttcgg   1740

aaagaaaaaa cactcttttc ttatcatagt aaagatattg atttggaagc attatctttt   1800

ttacaacagc attatcatgt taatttttat tcaatttcac caatgagccc tttgtctaaa   1860

cattttccta ttccaactgt agaggatgat tgtgaaacaa cttttgttgc gccactaaaa   1920

gaaaattaca ttaatgatat attgttgcct cctcattttg tatatgaaaa attagggacc   1980

atcgtgtcta agaaatcacg ttttcattct aacttgattg tcaggttgat tagagactta   2040

ttgaaattac cgagtgcact taaacactat ttaaaagaaa aacaccacca ccaccaccac   2100

taa                                                                 2103
```

<210> SEQ ID NO 19
<211> LENGTH: 897
<212> TYPE: DNA
<213> ORGANISM: Artificial Sequence
<220> FEATURE:
<223> OTHER INFORMATION: synthetic WTPmST3delta20-His-6
sialyltransferase fusion protein

<400> SEQUENCE: 19

```
atggataagt tcgcagaaca tgaaataccg aaagccgtta ttgttgcagg gaatggcgag     60

agtttaagtc aaattgatta taggttgtta ccgaaaaatt atgatgtgtt tcgttgtaat    120

caattttatt ttgaagaacg ctattttta ggaaacaaga taaaagcagt tttcttcacg    180

ccaggggtct ttcttgagca atattataca ctttatcatc tcaagagaaa caatgagtat    240

tttgttgata atgtgattct ctcttctttt aatcatccta cagtagattt agaaaagagt    300

cagaaaatac aagcactttt tattgatgtg atcaacggat atgaaaagta tttatctaaa    360
```

-continued

```
ctcactgctt ttgatgttta tttgcgctat aaagaattat atgagaatca aagaattaca    420

tctggcgtat atatgtgtgc agttgctatt gcgatgggat atacagatat ttacttaact    480

ggtatcgatt tttatcaagc gagcgaagaa aactacgcat tcgataataa aaagcctaac    540

attattaggt tattgcctga ttttcggaaa gaaaaaacac tcttttctta tcatagtaaa    600

gatattgatt tggaagcatt atctttttta caacagcatt atcatgttaa tttttattca    660

atttcaccaa tgagcccttt gtctaaacat tttcctattc caactgtaga ggatgattgt    720

gaaacaactt ttgttgcgcc actaaaagaa aattacatta atgatatatt gttgcctcct    780

cattttgtat atgaaaaatt agggaccatc gtgtctaaga aatcacgttt tcattctaac    840

ttgattgtcg tcgacaagct tgcggccgca ctcgagcacc accaccacca ccactga       897
```

<210> SEQ ID NO 20
<211> LENGTH: 852
<212> TYPE: DNA
<213> ORGANISM: Artificial Sequence
<220> FEATURE:
<223> OTHER INFORMATION: synthetic WTPmST3delta35-His-6
sialyltransferase fusion protein

<400> SEQUENCE: 20

```
atggataagt tcgcagaaca tgaaataccg aaagccgtta ttgttgcagg gaatggcgag     60

agtttaagtc aaattgatta taggttgtta ccgaaaaatt atgatgtgtt tcgttgtaat    120

caattttatt ttgaagaacg ctattttttta ggaaacaaga taaaagcagt tttcttcacg    180

ccaggggtct ttcttgagca atattataca ctttatcatc tcaagagaaa caatgagtat    240

tttgttgata atgtgattct ctcttctttt aatcatccta cagtagattt agaaaagagt    300

cagaaaatac aagcactttt tattgatgtg atcaacggat atgaaaagta tttatctaaa    360

ctcactgctt ttgatgttta tttgcgctat aaagaattat atgagaatca aagaattaca    420

tctggcgtat atatgtgtgc agttgctatt gcgatgggat atacagatat ttacttaact    480

ggtatcgatt tttatcaagc gagcgaagaa aactacgcat tcgataataa aaagcctaac    540

attattaggt tattgcctga ttttcggaaa gaaaaaacac tcttttctta tcatagtaaa    600

gatattgatt tggaagcatt atctttttta caacagcatt atcatgttaa tttttattca    660

atttcaccaa tgagcccttt gtctaaacat tttcctattc caactgtaga ggatgattgt    720

gaaacaactt ttgttgcgcc actaaaagaa aattacatta atgatatatt gttgcctcct    780

cattttgtat atgaaaaatt aggggtcgac aagcttgcgg ccgcactcga gcaccaccac    840

caccaccact ga                                                         852
```

<210> SEQ ID NO 21
<211> LENGTH: 821
<212> TYPE: DNA
<213> ORGANISM: Artificial Sequence
<220> FEATURE:
<223> OTHER INFORMATION: synthetic WTPmST3delta45-His-6
sialyltransferase fusion protein

<400> SEQUENCE: 21

```
atggataagt tcgcagaaca tgaaataccg aaagccgtta ttgttgcagg gaatggcgag     60

agtttaagtc aaattgatta taggttgtta ccgaaaaatt atgatgtgtt tcgttgtaat    120

caattttatt ttgaagaacg ctattttttta ggaaacaaga taaaagcagt tttcttcacg    180

ccaggggtct ttcttgagca atattataca ctttatcatc tcaagagaaa caatgagtat    240

tttgttgata atgtgattct ctcttctttt aatcatccta cagtagattt agaaaagagt    300
```

-continued

```
cagaaaatac aagcactttt tattgatgtg atcaacggat atgaaaagta tttatctaaa    360

ctcactgctt ttgatgttta tttgcgctat aaagaattat atgagaatca aagaattaca    420

tctggcgtat atatgtgtgc agttgctatt gcgatgggat atacagatat ttacttaact    480

ggtatcgatt tttatcaagc gagcgaagaa aactacgcat tcgataataa aaagcctaac    540

attattaggt tattgcctga ttttcggaaa gaaaaaacac tcttttctta tcatagtaaa    600

gatattgatt tggaagcatt atcttttttta caacagcatt atcatgttaa tttttattca    660

atttcaccaa tgagcccttt gtctaaacat tttcctattc caactgtaga ggatgattgt    720

gaaacaactt ttgttgcgcc actaaaagaa aattacatta atgatatatt gttggtcgac    780

aagcttgcgg ccgcactcga gcaccaccac caccaccatg a                        821
```

<210> SEQ ID NO 22
<211> LENGTH: 1424
<212> TYPE: DNA
<213> ORGANISM: Pasteurella multocida
<220> FEATURE:
<223> OTHER INFORMATION: Pasteurella multocida strain Pm70 GT42 family monofunctional alpha2-3-sialyltransferase Pm1174

<400> SEQUENCE: 22

```
tcacaatcgc ttcaaataat ggggtcatat cttctgctaa atcatcgtgt tcaagacccg     60

caacaccatt taatgcagaa gcataaataa ttggaaaatc taactgctca tcagttgcac    120

ctaagttgac aaaaagatca aaaacttgat ccactaccca gtcagggcgc gcgcccggac    180

ggtcaacttt gttgatcacc acaattggtt ttaaaccgtg ggcaaacgct ttttgagtca    240

caaaacgcgt ttgtggcatt ggaccatcaa aagcatctac aattaaaagt acacaatcta    300

ccattgacat cacacgttcc acttcaccac cgaagtctgc gtgtcctggg gtgtctacga    360

tattaatgcg atagtcattc caattaatgg cggtattctt agctaaaatg gtaataccac    420

gttctttttc gatgtcatta gagtccatga cacgctcatc actttcatta cgtgatgcct    480

ctaatgtgcc ggattgttgt aaaagtttat caacgagggt agttttaccg tggtcaacgt    540

gggcgataat tgcgatatta cgcaatttat tgatatctat tttatctgtc attgagaaaa    600

tcttatatat tgaaatagga aaaagttctt tttctgaccg cacttttagc gaaaaagtgt    660

gtgaaagggg caagattata caacagatcc tccccctaga gccataaaaa ctgctatttt    720

tcttttaaat agtgtttaag tgcactcggt atttcatgtt ctgcgaactt atccatctct    780

cctccactaa tttattatag tgcataatcc atgtattcta cacgaaataa agtgtaggga    840

tatatccgaa aaacacgaat aaaatactag atttatagta taacttttat tatattgaat    900

tcttttaaat acgcttctaa cactaaggat cctctatgtc agacaccacc gctatcgcca    960

acgtattcaa gctgattgaa gaatacgata tcaaatttgt tttacttcgc tttaccgata   1020

ttaaggggaa agaacacggt gtttcgcttc ctgttaatct tgttgatgaa gatttatttg   1080

aagacggtaa aatgttcgac ggttcttccg ttgaaggatg gaaggcaatc aataaagcag   1140

atatgctctt gatgccaatg ccagaaacag ctgtggttga tccttttgct caaattccta   1200

ccctttccct ccgttgcagt atctacgaac cttctactat gcaaagctac gatcgtgatc   1260

cacgttctat tgcgattcgt gcagaaaact atatgcgttc aacgggaata gccgatgaag   1320

ccctctttgg gcctgaacca gaatttttct tatttgatga tgttcgtttc gatgtctcga   1380

tgaaccgtag cagttattct gttgatgata ttgaggctgc gtgg                    1424
```

-continued

<210> SEQ ID NO 23
<211> LENGTH: 1200
<212> TYPE: DNA
<213> ORGANISM: Pasteurella multocida
<220> FEATURE:
<223> OTHER INFORMATION: Pasteurella multocida A:3 strain P-1059
alpha2-3-sialyltransferase

<400> SEQUENCE: 23

```
gttcagaccc gcaacaccat ttaatgcgga agcataaata attggaaaat ctaactggtc     60

atcggttgca cctaagttga caaaaagatc aaagacttga tccactaccc agtcaggacg    120

cgcgccagga cggtcaactt tgttgatcac cactattggt tttaaaccgt gggcaaacgc    180

tttttgagtc acaaaacgcg tttgtggcat tggaccatca aaagcatcta caattaaaag    240

tacacaatct accattgaca tcacacgttc tacttcacca ccgaagtctg cgtgtcctgg    300

ggtgtctacg atattaatgc gatagtcatt ccaattaatg gcggtattct tagctaaaat    360

ggtaatacca cgttcttttt cgatgtcatt agagtccatg acacgctcat cactttcatt    420

acgtgatgcc tctaatgtgc cggattgttg taaaagttta tcaacgaggg tagttttacc    480

gtggtcaacg tgggcgataa ttgcgatatt acgcaattta ttgatatcta ttttatctgt    540

cattgagaaa atcttatata ttgaaatagg aaaaagttct ttttctgacc gcacttttag    600

cgaaaaagtg tgtgaaaggg gcaagattat acaacttttt acgccaagga gccattaaat    660

aatcactgaa aaaacacata aaaattctgt atttcccaac gactgtttta taatactttt    720

ttattctact cccccaaact aacaggattt cttatatgcc aaacacagtt gctatcgcca    780

acgtattcaa gctgattgaa gaatacaata tcaaatttgt tttacttcgc tttaccgata    840

ttaaggggaa agaacacggt gtttcgcttc ctgttaatct tgttgatgaa gatttatttg    900

aagacggtaa aatgttcgac ggttcttccg ttgaaggatg gaaggcaatc aataaagcag    960

atatgctctt gatgccaatg ccagaaacag ctgtggttga tccttttgct caaattccta   1020

ccctttccct ccgttgcagt atctacgaac cttctactat gcaaagctac gatcgtgatc   1080

cacgttctat tgcgattcgt gccgaaaact atatgcgttc aacgggaata gccgatgaag   1140

ccctctttgg acctgaacca gaatttttct tatttgatga tgttcgtttc gatgtctcga   1200
```

<210> SEQ ID NO 24
<211> LENGTH: 1207
<212> TYPE: DNA
<213> ORGANISM: Pasteurella multocida
<220> FEATURE:
<223> OTHER INFORMATION: Pasteurella multocida serogroup D strain P-934
alpha2-3-sialyltransferase

<400> SEQUENCE: 24

```
catcgtgttc agacccgcaa caccatttaa tgcggaagca taaataattg gaaaatctaa     60

ctgctcatcg gttgcaccta agttgacaaa aagatcaaaa acttgatcca ctacccagtc    120

aggacgcgcg ccaggacggt caactttgtt aatcaccaca attggtttta aaccgtgggc    180

aaacgctttt tgagtcacaa aacgcgtttg tggcattgga ccatcaaaag catctacaat    240

taaaagtaca caatctacca ttgacatcac acgttctact tcaccaccga agtctgcgtg    300

tcctggggtg tctacgatat taatgcgata gtcattccaa ttaatggcgg tattcttagc    360

taaaatggta ataccacgtt ctttttcgat gtcattagag tccatgacac gctcatcact    420

ttcattacgt gatgcctcta atgtgccgga ttgttgtaaa agtttatcaa cgagggtagt    480

tttaccgtgg tcaacgtggg cgataattgc gatattacgc aatttattga tatctatttt    540
```

```
atctgtcatt gagaaaatct tatatattga aataggaaaa agttcttttt ctgaccgcac    600

ttttagcgaa aaagtgtgtg aaaggggcaa gattatacaa ctttttacgc caaggagcca    660

ttaaataatc actgaaaaaa cacataaaaa ttctgtattt cccaacgact gttttataat    720

actttttat tctactcccc caaactaaga ggatttctta tatgccaaac acagttgcta     780

tcgccaacgt attcaagctg attgaagaat acgatatcaa atttgtttta cttcgcttta    840

ccgatattaa ggggaaagaa cacggtgttt cgcttcctgt taatcttgtt gatgaagatt    900

tatttgaaga cggtaaaatg ttcgacggtt cttccgttga aggatggaag gcaatcaata    960

aaccagatat gctcttgatg ccaatgccag aaacagctgt ggttgatcct tttgctcaaa   1020

ttcctaccct ttccctccgt tgcagtatct acgaaccttc tactatgcaa agctacgatc   1080

gtgatccacg ttctattgcg attcgtgccg aaaactatat gcgttcaacg ggaatagccg   1140

atgaagccct ctttggacct gagccagaat ttttcttatt tgatgatgtt cgtttcgatg   1200

tctcgat                                                             1207
```

```
<210> SEQ ID NO 25
<211> LENGTH: 300
<212> TYPE: PRT
<213> ORGANISM: Campylobacter jejuni
<220> FEATURE:
<223> OTHER INFORMATION: amino acids 1-300 of monofunctional alpha2-3-
      sialyltransferase CstI

<400> SEQUENCE: 25

Met Thr Arg Thr Arg Met Glu Asn Glu Leu Ile Val Ser Lys Asn Met
 1               5                   10                  15

Gln Asn Ile Ile Ile Ala Gly Asn Gly Pro Ser Leu Lys Asn Ile Asn
            20                  25                  30

Tyr Lys Arg Leu Pro Arg Glu Tyr Asp Val Phe Arg Cys Asn Gln Phe
        35                  40                  45

Tyr Phe Glu Asp Lys Tyr Tyr Leu Gly Lys Lys Ile Lys Ala Val Phe
    50                  55                  60

Phe Asn Pro Gly Val Phe Leu Gln Gln Tyr His Thr Ala Lys Gln Leu
65                  70                  75                  80

Ile Leu Lys Asn Glu Tyr Glu Ile Lys Asn Ile Phe Cys Ser Thr Phe
                85                  90                  95

Asn Leu Pro Phe Ile Glu Ser Asn Asp Phe Leu His Gln Phe Tyr Asn
            100                 105                 110

Phe Phe Pro Asp Ala Lys Leu Gly Tyr Glu Val Ile Glu Asn Leu Lys
        115                 120                 125

Glu Phe Tyr Ala Tyr Ile Lys Tyr Asn Glu Ile Tyr Phe Asn Lys Arg
    130                 135                 140

Ile Thr Ser Gly Val Tyr Met Cys Ala Ile Ala Ile Ala Leu Gly Tyr
145                 150                 155                 160

Lys Thr Ile Tyr Leu Cys Gly Ile Asp Phe Tyr Glu Gly Asp Val Ile
                165                 170                 175

Tyr Pro Phe Glu Ala Met Ser Thr Asn Ile Lys Thr Ile Phe Pro Gly
            180                 185                 190

Ile Lys Asp Phe Lys Pro Ser Asn Cys His Ser Lys Glu Tyr Asp Ile
        195                 200                 205

Glu Ala Leu Lys Leu Leu Lys Ser Ile Tyr Lys Val Asn Ile Tyr Ala
    210                 215                 220

Leu Cys Asp Asp Ser Ile Leu Ala Asn His Phe Pro Leu Ser Ile Asn
225                 230                 235                 240
```

```
Ile Asn Asn Asn Phe Thr Leu Glu Asn Lys His Asn Asn Ser Ile Asn
                245                 250                 255

Asp Ile Leu Leu Thr Asp Asn Thr Pro Gly Val Ser Phe Tyr Lys Asn
            260                 265                 270

Gln Leu Lys Ala Asp Asn Lys Ile Met Leu Asn Phe Tyr Asn Ile Leu
        275                 280                 285

His Ser Lys Asp Asn Leu Ile Lys Phe Leu Asn Lys
    290                 295                 300


<210> SEQ ID NO 26
<211> LENGTH: 291
<212> TYPE: PRT
<213> ORGANISM: Campylobacter jejuni
<220> FEATURE:
<223> OTHER INFORMATION: multifunctional alpha2-3/8-sialyltransferase
      CstII with alpha2-8-sialidase and alpha2-8-trans-sialisdase
      activities

<400> SEQUENCE: 26

Met Lys Lys Val Ile Ile Ala Gly Asn Gly Pro Ser Leu Lys Glu Ile
 1               5                  10                  15

Asp Tyr Ser Arg Leu Pro Asn Asp Phe Asp Val Phe Arg Cys Asn Gln
            20                  25                  30

Phe Tyr Phe Glu Asp Lys Tyr Tyr Leu Gly Lys Lys Cys Lys Ala Val
        35                  40                  45

Phe Tyr Asn Pro Ile Leu Phe Phe Glu Gln Tyr Tyr Thr Leu Lys His
    50                  55                  60

Leu Ile Gln Asn Gln Glu Tyr Glu Thr Glu Leu Ile Met Cys Ser Asn
65                  70                  75                  80

Tyr Asn Gln Ala His Leu Glu Asn Glu Asn Phe Val Lys Thr Phe Tyr
                85                  90                  95

Asp Tyr Phe Pro Asp Ala His Leu Gly Tyr Asp Phe Phe Lys Gln Leu
            100                 105                 110

Lys Asp Phe Asn Ala Tyr Phe Lys Phe His Glu Ile Tyr Phe Asn Gln
        115                 120                 125

Arg Ile Thr Ser Gly Val Tyr Met Cys Ala Val Ala Ile Ala Leu Gly
    130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190

Asp Ile Lys Ala Leu Glu Phe Leu Glu Lys Thr Tyr Lys Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe Lys Lys Ile Lys Ile Lys Glu Asn Ile Tyr Tyr Lys
            260                 265                 270

Leu Ile Lys Asp Leu Leu Arg Leu Pro Ser Asp Ile Lys His Tyr Phe
        275                 280                 285
```

```
Lys Gly Lys
    290


<210> SEQ ID NO 27
<211> LENGTH: 332
<212> TYPE: PRT
<213> ORGANISM: Haemophilus influenzae
<220> FEATURE:
<223> OTHER INFORMATION: lipopolysaccharide bifunctional
      alpha2-3/8-sialyltransferase Lic3B

<400> SEQUENCE: 27

Met Pro Asn Gln Ser Ile Asn Gln Ser Ile Asn Gln Ser Ile Asn Gln
 1               5                  10                  15

Ser Ile Asn Gln Ser Ile Asn Gln Ser Ile Asn Gln Ser Ile Asn Gln
            20                  25                  30

Ser Ile Asn Gln Ser Lys Pro Val Ile Ile Ala Gly Asn Gly Thr Ser
        35                  40                  45

Leu Lys Ser Ile Asp Tyr Ser Leu Leu Pro Lys Asp Tyr Asp Val Phe
    50                  55                  60

Arg Cys Asn Gln Phe Tyr Phe Glu Asp His Tyr Phe Leu Gly Lys Lys
65                  70                  75                  80

Ile Lys Lys Val Phe Phe Asn Cys Ser Val Ile Phe Glu Gln Tyr Tyr
                85                  90                  95

Thr Phe Met Gln Leu Ile Lys Asn Asn Glu Tyr Glu Tyr Ala Asp Ile
            100                 105                 110

Ile Leu Ser Ser Phe Leu Asn Leu Gly Asp Ser Glu Leu Lys Lys Ile
        115                 120                 125

Gln Arg Leu Glu Lys Leu Leu Pro Gln Ile Asp Leu Gly His Ser Tyr
    130                 135                 140

Leu Lys Lys Leu Arg Ala Phe Asp Ala His Leu Gln Tyr His Glu Leu
145                 150                 155                 160

Tyr Glu Asn Lys Arg Ile Thr Ser Gly Val Tyr Met Cys Ala Val Ala
                165                 170                 175

Thr Ala Met Gly Tyr Lys Asp Leu Tyr Leu Thr Gly Ile Asp Phe Tyr
            180                 185                 190

Gln Glu Lys Gly Asn Pro Tyr Ala Phe His His Gln Lys Glu Asn Ile
        195                 200                 205

Ile Lys Leu Leu Pro Ser Phe Ser Gln Asn Lys Ser Gln Asn Asp Ile
    210                 215                 220

His Ser Met Glu Tyr Asp Leu Asn Ala Leu Tyr Phe Leu Gln Lys His
225                 230                 235                 240

Tyr Gly Val Asn Ile Tyr Cys Ile Ser Pro Glu Ser Pro Leu Cys Asn
                245                 250                 255

Tyr Phe Pro Leu Ser Pro Leu Asn Asn Pro Phe Thr Phe Ile Pro Glu
            260                 265                 270

Glu Lys Lys Asn Tyr Thr Gln Asp Ile Leu Ile Pro Pro Glu Ser Val
        275                 280                 285

Tyr Lys Lys Ile Gly Ile Tyr Ser Lys Pro Arg Ile Tyr Gln Asn Leu
    290                 295                 300

Val Phe Arg Leu Ile Trp Asp Ile Leu Arg Leu Pro Asn Asp Ile Lys
305                 310                 315                 320

Lys Ala Leu Lys Ala Lys Lys Met Arg Leu Arg Lys
                325                 330


<210> SEQ ID NO 28
```

<211> LENGTH: 35
<212> TYPE: DNA
<213> ORGANISM: Artificial Sequence
<220> FEATURE:
<223> OTHER INFORMATION: synthetic PCR amplification primer 5'-pET22b-PmST3

<400> SEQUENCE: 28
gatccatatg gataaatttg ccgaacatga aattc 35

<210> SEQ ID NO 29
<211> LENGTH: 33
<212> TYPE: DNA
<213> ORGANISM: Artificial Sequence
<220> FEATURE:
<223> OTHER INFORMATION: synthetic PCR amplification primer 3'-pET22b-PmST3

<400> SEQUENCE: 29
ccgctcgagt ttttctttca gataatgttt cag 33

<210> SEQ ID NO 30
<211> LENGTH: 35
<212> TYPE: DNA
<213> ORGANISM: Artificial Sequence
<220> FEATURE:
<223> OTHER INFORMATION: synthetic PCR amplification primer 3'-pET22b-PmST3delta20

<400> SEQUENCE: 30
cagcgtcgac cacaatcaga ttgctatgaa aacgg 35

<210> SEQ ID NO 31
<211> LENGTH: 37
<212> TYPE: DNA
<213> ORGANISM: Artificial Sequence
<220> FEATURE:
<223> OTHER INFORMATION: synthetic PCR amplification primer 3'-pET22b-PmST3delta35

<400> SEQUENCE: 31
cagcgtcgac gcccagtttt tcatacacaa aatgcgg 37

<210> SEQ ID NO 32
<211> LENGTH: 37
<212> TYPE: DNA
<213> ORGANISM: Artificial Sequence
<220> FEATURE:
<223> OTHER INFORMATION: synthetic PCR amplification primer 3'-pET22b-PmST3delta45

<400> SEQUENCE: 32
cagcgtcgac cagcagaata tcattaatat aattttc 37

<210> SEQ ID NO 33
<211> LENGTH: 38
<212> TYPE: DNA
<213> ORGANISM: Artificial Sequence
<220> FEATURE:
<223> OTHER INFORMATION: synthetic PCR amplification primer 5'-pMAL-c4X-PmST3

<400> SEQUENCE: 33
gaccgaattc atggataaat ttgccgaaca tgaaattc 38

<210> SEQ ID NO 34
<211> LENGTH: 55

-continued

```
<212> TYPE: DNA
<213> ORGANISM: Artificial Sequence
<220> FEATURE:
<223> OTHER INFORMATION: synthetic PCR amplification primer 3'-pMAL-c4X-
      PmST3

<400> SEQUENCE: 34

gatcaagctt ttagtggtgg tggtggtggt gtttttcttt cagataatgt ttcag         55


<210> SEQ ID NO 35
<211> LENGTH: 36
<212> TYPE: DNA
<213> ORGANISM: Artificial Sequence
<220> FEATURE:
<223> OTHER INFORMATION: synthetic PCR cloning forward primer
      corresponding to internal sequence of Pm1173 gene

<400> SEQUENCE: 35

gatccatatg tcacaatcgc ttcaaataat ggggtc                              36


<210> SEQ ID NO 36
<211> LENGTH: 35
<212> TYPE: DNA
<213> ORGANISM: Artificial Sequence
<220> FEATURE:
<223> OTHER INFORMATION: synthetic PCR cloning reverse primer
      corresponding to internal sequence of Pm1175 gene

<400> SEQUENCE: 36

ccgctcgagc cacgcagcct caatatcatc aacag                               35


<210> SEQ ID NO 37
<211> LENGTH: 6
<212> TYPE: PRT
<213> ORGANISM: Artificial Sequence
<220> FEATURE:
<223> OTHER INFORMATION: synthetic C-terminal His-6 tag

<400> SEQUENCE: 37

His His His His His His
 1               5
```